US010557803B2

(12) United States Patent
Lynch

(10) Patent No.: US 10,557,803 B2
(45) Date of Patent: Feb. 11, 2020

(54) SURFACE HEIGHT DETERMINATION OF TRANSPARENT FILM

(71) Applicant: Nanometrics Incorporated, Milpitas, CA (US)

(72) Inventor: Graham M. Lynch, Singapore (SG)

(73) Assignee: Onto Innovation Inc., Wilmington, MA (US)

( * ) Notice: Subject to any disclaimer, the term of this patent is extended or adjusted under 35 U.S.C. 154(b) by 0 days.

(21) Appl. No.: 16/113,165

(22) Filed: Aug. 27, 2018

(65) Prior Publication Data

US 2019/0391088 A1 Dec. 26, 2019

Related U.S. Application Data

(60) Provisional application No. 62/690,230, filed on Jun. 26, 2018.

(51) Int. Cl.
| | |
|---|---|
| *G01N 21/956* | (2006.01) |
| *G01N 21/95* | (2006.01) |
| *G01N 21/88* | (2006.01) |
| *G01B 11/06* | (2006.01) |

(52) U.S. Cl.
CPC ... *G01N 21/95607* (2013.01); *G01B 11/0608* (2013.01); *G01B 11/0675* (2013.01); *G01N 21/8806* (2013.01); *G01N 21/9501* (2013.01); *G01N 2021/8845* (2013.01); *G01N 2021/95615* (2013.01)

(58) Field of Classification Search
CPC ............. G01N 21/95607; G01N 21/88; G01N 21/9501; G01B 11/06
See application file for complete search history.

(56) References Cited

U.S. PATENT DOCUMENTS

| | | | |
|---|---|---|---|
| 4,330,712 A | * | 5/1982 | Yoshida ........... G01N 21/95607 250/559.39 |
| 5,398,113 A | | 3/1995 | de Groot |
| 5,677,765 A | | 10/1997 | Laird et al. |
| 6,753,972 B1 | | 6/2004 | Hirose et al. |

(Continued)

OTHER PUBLICATIONS

International Search Report and Written Opinion dated Aug. 12, 2019 from PCT application No. PCT/US2019/035587, filed Jun. 5, 2019.

*Primary Examiner* — Maurice C Smith
(74) *Attorney, Agent, or Firm* — Paradice and Li LLP

(57) ABSTRACT

A surface topography of a sample with a transparent surface layer is measured using surface topographies of a reference sample. The surface topographies of the reference sample are measured before and after the deposition of an opaque film over the surface layer. A surface topography of the sample is measured at the same relative positions as the surface topography measurements of the reference sample. A height difference at multiple corresponding positions on the sample and the pre-opaque film reference sample is determined. The actual surface height of the reference sample at each position is known from the surface topography of the post-opaque reference sample. The actual surface topography of the sample is determined by combining the actual surface heights of the reference sample with the determined height differences. The resulting surface topography of the sample may be used to characterize the sample, such as detecting defects on the sample.

23 Claims, 11 Drawing Sheets

(56) References Cited

U.S. PATENT DOCUMENTS

| | | | |
|---|---|---|---|
| 6,999,180 B1 | 2/2006 | Janik et al. | |
| 7,177,030 B2 | 2/2007 | Leizerson et al. | |
| 8,818,754 B2 * | 8/2014 | Kamenev | G01B 11/0675 |
| | | | 702/167 |
| 8,825,444 B1 * | 9/2014 | Rovira | G05B 23/024 |
| | | | 702/104 |
| 9,989,477 B2 | 6/2018 | Vaez-Iravani et al. | |
| 2005/0088663 A1 | 4/2005 | De Groot et al. | |
| 2017/0178980 A1 | 6/2017 | Owen et al. | |

* cited by examiner

US 10,557,803 B2

SURFACE HEIGHT DETERMINATION OF TRANSPARENT FILM

CROSS REFERENCE TO RELATED APPLICATIONS

This application claims priority under 35 USC 119 to U.S. Provisional Application No. 62/690,230, entitled "ABSOLUTE HEIGHT DETERMINATION OF TRANSPARENT FILM," filed Jun. 26, 2018, which is incorporated herein by reference in its entirety.

FIELD OF THE INVENTION

The present invention is related to optical metrology, and in particular to optical metrology capable of height determination or defect detection on a sample.

BACKGROUND

Semiconductor and other similar industries, often use optical metrology equipment to provide non-contact evaluation of substrates during processing. One type of optical metrology device is an interferometer which superimposes electromagnetic waves, e.g., light, reflected from a reference surface and a sample surface resulting in interference from which information about the sample may be extracted. Interferometers are capable of measuring small height differences on a sample. Interferometers, for example, are sometimes used to detect defects, e.g., by comparing a measured height to reference height, where measured height that is much greater or lesser than the reference height may indicate a defect. Other optical metrology devices may measure characteristics of a sample from light that is reflected off of the surface of the sample.

Interferometry and many other optical metrology techniques rely on the reflection of light from the surface of the sample. Semiconductor processing, however, often uses layers that are at least partially transparent to specific wavelengths of light. An accurate measurement of a sample with a layer that is at least partially transparent to the wavelengths of light used by the optical metrology device is difficult.

SUMMARY

A surface topography of a sample having an at least partially transparent surface layer is measured using surface topographies of reference sample that is nominally the same as the sample. The surface topographies of the reference sample are measured before and after the deposition of an opaque, reflective film over the surface layer. The surface topography of the sample is measured at the same positions, e.g., at same XY positions on the wafer, or same within-die coordinates, as the surface topography measurements on the reference sample so that any underlying patters at the measurement locations are the same. A relative height difference between measured surface heights at multiple corresponding positions on the sample and the pre-opaque film reference sample is determined. The actual surface height of the reference sample at each position is known from the surface topography of the post-opaque reference sample. The actual surface height on the sample is produced by combining the actual surface height of the reference sample with the relative height differences between the reference sample and the sample. The resulting surface topography of the sample may be used to characterize the sample, such as detecting defects. For example, surface heights may be compared to a predetermined defect threshold or to a Depth of Focus window of a process tool to determine whether defects are present on the sample, or may be used to determine characteristics such as warp, bow, large scale three-dimensional (3D) surface topology, or micro-scale 3D surface topology.

In one aspect, a method of characterizing a test sample that is a semiconductor sample includes measuring with an optical metrology device a first surface topography of at least one reference sample having a surface film that is at least partially transparent to one or more wavelengths of light used by the optical metrology device, wherein the first surface topography comprises a first relative height of a top surface of the at least one reference sample at each pixel in a first plurality of pixels on the at least one reference sample; measuring with the optical metrology device a second surface topography of the at least one reference sample after an opaque film is deposited over the surface film, wherein the opaque film is opaque to the one or more wavelengths of light used by the optical metrology device, wherein the second surface topography comprises a second relative height of the top surface of the at least one reference sample at each pixel in the first plurality of pixels; storing the first surface topography and the second surface topography of the at least one reference sample and a position of each pixel in the first plurality of pixels on the at least one reference sample; measuring with the optical metrology device a third surface topography of the test sample, wherein the test sample is nominally the same as the at least one reference sample and includes a surface film that is at least partially transparent to the one or more wavelengths of light used by the optical metrology device and does not include an opaque film deposited over the surface film, wherein the third surface topography comprises a third relative height of a top surface of the test sample at each pixel in a second plurality of pixels on the test sample, wherein a position of each pixel in the second plurality of pixels on the test sample is the same as the position of each pixel in the first plurality of pixels on the at least one reference sample; determining a differential surface topography by comparing the first surface topography to the third surface topography; determining a proxy surface topography of the test sample by combining the differential surface topography with the second surface topography, wherein the proxy surface topography comprises a fourth relative height of the top surface of the test sample at each pixel in the second plurality of pixels on the test sample; determining the characteristic of the test sample with the proxy surface topography of the test sample; and communicating a signal to a process tool that causes the process tool to adjust a process parameter associated with a fabrication process step of the sample fabrication sequence based on the characteristic of the test sample.

In one aspect, an optical metrology apparatus configured to characterize a test sample that is a semiconductor sample includes a light source that produces an illumination beam; an objective lens that directs the illumination beam to be incident on a sample and to receive light reflected by the sample, at least one detector array that receives the light after it is reflected by the sample and acquires optical metrology data from the light; and at least one processor coupled to the at least one detector array, the at least one processor configured to: obtain a first surface topography of at least one reference sample and a second surface topography of the at least one reference sample, wherein the at least one reference sample has a surface film that is at least partially transparent to one or more wavelengths of light in the illumination beam, the first surface topography comprises a first relative height of a top surface of the at least one reference sample at each pixel in a first plurality of pixels on the at least one reference sample, and the second surface topography of the at least one reference sample comprises a second relative height of the top surface of the at least one reference sample at each pixel in the first plurality of pixels after an opaque film is deposited over the surface film, wherein the opaque film is opaque to the one or more wavelengths of light used by the optical metrology device; measuring a third surface topography of a test sample, wherein the test sample is nominally the same as the at least one reference sample and includes a surface film that is at least partially transparent to the one or more wavelengths of light in the illumination beam and does not include an opaque film deposited over the surface film, wherein the third surface topography comprises a third relative height of a top surface of the test sample at each pixel in a second plurality of pixels on the test sample, wherein a position of each pixel in the second plurality of pixels on the test sample is the same as the position of each pixel in the first plurality of pixels on the at least one reference sample; determine a differential surface topography by comparing the first surface topography to the third surface topography; determine a proxy surface topography of the test sample by combining the differential surface topography with the second surface topography, wherein the proxy surface topography comprises a fourth relative height of the top surface of the test sample at each pixel in the second plurality of pixels on the test sample; determine the characteristic of the test sample with the proxy surface topography of the test sample; and communicate a signal to a process tool that causes the process tool to adjust a process parameter associated with a fabrication process step of the sample fabrication sequence based on the characteristic of the test sample.

DESCRIPTION

An accurate measurement of the surface topography of a test sample, which has an at least partially transparent surface layer, is accomplished using a reference sample that is nominally the same as the test sample. The surface topography of the reference sample, e.g., surface height measurements at a plurality of positions on the reference sample, is measured twice, before and after the deposition of an opaque, reflective film over the at least partially transparent top layer. The surface topography of the test sample is also measured at the same relative positions on the sample. Because the surface layers of the reference sample and test sample is at least partially transparent to the light used by the optical metrology device, the measured surface heights at each position are not strongly correlated to the actual surface heights at those positions because patterns and films underlying the transparent surface layer may contribute more to the measurement than the actual height of the top surface. The relative height difference between the measured surface heights at the same positions on the test sample and pre-opaque film reference sample, however, are strongly correlated to the actual height differences of the top surface between the reference sample and test sample at corresponding positions. The actual surface height at each position on the reference sample is known from the post-opaque film surface topography measurement. Accordingly, actual surface height at each position on the reference sample may be combined with the relative height differences between the reference sample and the test sample to determine the actual surface height at each position of the test sample, i.e., the actual surface topography of the test sample. The resulting surface topography of the test sample may be used to characterize the test sample, such as detecting defects, warp, bow, large scale three-dimensional (3D) or micro-scale 3D surface topology, or other such characteristics, which may be used to modify, alter, or inform further processing of the test sample or the processing of subsequently processed samples, e.g., in a feed forward or feedback process.

Figure 1:
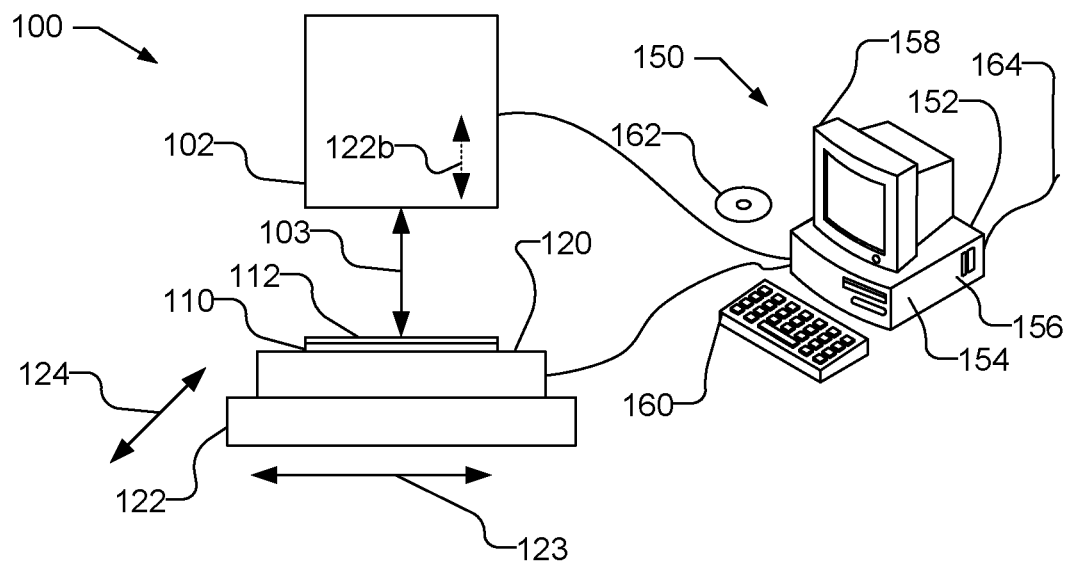
FIG. 1 illustrates an optical metrology device that may be used to measure the surface topography of a sample.

FIG. 1 shows a schematic view of an optical metrology device 100 that may be used to measure the surface height of a sample 110, e.g., using the process disclosed herein. The metrology device 100, for example, may be an interferometer, as discussed herein. In addition, the optical metrology device 100 may be, e.g., a Confocal Optical Microscope, which may measure relative-surface-heights, e.g., relative between two different X-Y coordinates for the same tool/sample. In addition to interferometry and Confocal Optical microscopy, Optical-CD (in-die in Array areas) may be used with the process described herein.

As illustrated, metrology device 100 includes an optical head 102 and a stage 122 that positions the sample 110, which is held on chuck 120, for measurement under the optical head 102. The stage 122, for example, is capable of horizontal motion in either Cartesian (i.e., X and Y) coordinates, as indicated by arrows 123 and 124, or Polar (i.e., R and θ) coordinates or some combination of the two and optionally capable of vertical motion. Alternatively, or additionally, a stage (not shown) may move the optical head 102 relative to the chuck 120, or both the optical head 102 and the chuck 120 may move, to position the sample 110 relative to the optical head 102 for measurement. Thus, the chuck 120 may be held stationary while the optics in the optical head 102 move relative to the sample 110 or both may move relative to the other. For example, the optical head 102 or a portion of the optical head 102, e.g., an objective lens, may be movable in the vertical direction, as indicated by arrow 122b.

As illustrated, the optical head 102 of the metrology device 100 is coupled to a computer system 150, such as a workstation, a personal computer, central processing unit or other adequate computer system, or multiple systems. If desired, multiple optical heads, i.e., different metrology devices such as a reflectometer, scatterometer, ellipsometer, etc., may be combined in the same metrology device 100 and coupled to computer system 150 so that multiple measurements may be combined with the surface height measurements if desired. The computer system 150 or multiple coupled computers may control the operation of the chuck 110, the stage 122 and optical head 102 and collect and analyze the data from the optical head 102 as discussed herein. A computer system 150 is preferably included in, is connected to, or is otherwise associated with optical head 102 for processing data detected by the optical head 102, as discussed herein. The computer system 150, which includes one or more processors 152 with memory 154 and storage 156, as well as a user interface including e.g., a display 158 and input devices 160. A non-transitory computer-usable storage medium 162 having computer-readable program code embodied may be used by the computer system 150 for causing the processor to control the metrology device 100 and to perform the functions including the analysis described herein. Moreover, the non-transitory computer-usable storage medium 162, storage 156 and/or memory 154 may store the reference sample data, as discussed herein. The data structures and software code for automatically implementing one or more acts described in this detailed description can be implemented by one of ordinary skill in the art in light of the present disclosure and stored, e.g., on a computer readable storage medium 162, which may be any device or medium that can store code and/or data for use by a computer system such as processor 152. The computer-usable storage medium 162 may be, but is not limited to, magnetic and optical storage devices such as disk drives, magnetic tape, compact discs, and DVDs (digital versatile discs or digital video discs). A communication port 164 may also be used to receive instructions that are used to program the computer system 150 to perform any one or more of the functions described herein and may represent any type of communication connection, such as to the internet or any other computer network. The communication port 164 may further export signals, e.g., with measurement results and/or instructions, to another system, such as external process tools, in a feed forward or feedback process in order to adjust a process parameter associated with a fabrication process step of the samples based on the measurement results. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Figure 2:
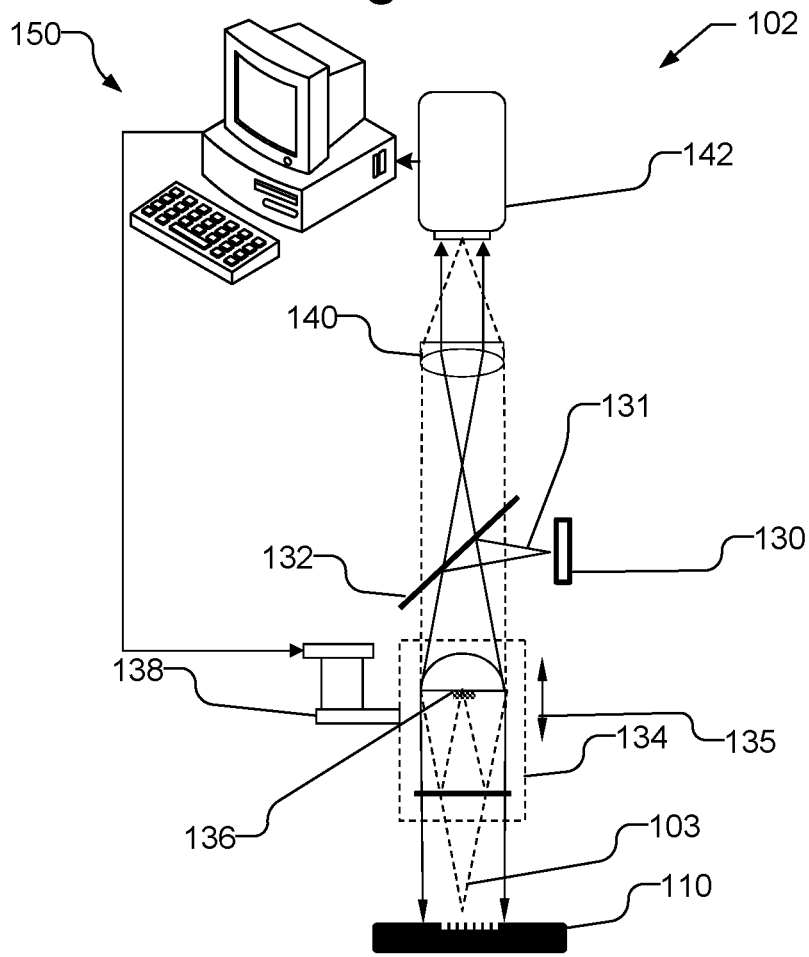
FIG. 2 illustrates an interferometer type optical head that may be used to measure the surface topography of a sample.

FIG. 2 illustrates one embodiment of an interferometer type optical head 102. As illustrated, the optical head 102 includes a light source 130 that provides a broadband or narrow band light beam 131. The light source 130, for example, may produce wavelengths of light in UV, blue, visible, or IR ranges. As discussed herein, one or more wavelengths of the light produced by the light source 130, however, is transmitted through the at least partially transparent surface layer. The particular wavelengths that will be transmitted through the surface layer are a function of the material and thickness of the surface layer, which is well understood in the art. A beam splitter 132 directs light beam 131, e.g., reflects light beam 131, towards an interference objective 134 that includes a reference mirror 136. The interference objective 134 is coupled to an actuator 138, which is controlled by the computer system 150, to adjust the vertical position (Z height) of the interference objective 134. The interference objective produces a probe beam 103 that is incident on and reflects from the sample 110, passes back through the interference objective 134 and beam splitter 132 and is focused by imaging lens 140 onto detector 142, which is coupled to the computer system 150. The resulting interference patterns, sometimes referred to interference signals, may be used to determine a surface height (sometimes referred to as Z-height) at the measurement position (sometimes referred to as a pixel) on the sample 110. The surface topography of the surface of the sample 110 may be determined by moving the sample 110 via stage 122 (or the optical head 102) to different measurement positions (pixels) and measuring the surface height at each position.

By scanning and measuring the Z-height for a plurality of pixels, the surface topography of the sample 110 can be measured.

It should be understood that the surface height measured at each position on the sample 110 is a relative surface height, e.g., determined by the Z-height of the interference objective 134. An absolute surface height of the sample may be determined, if desired, e.g., based on a known height between, e.g., the interference objective 134 and another object with a fixed position, such as the top surface of the chuck 120, surface of the earth, etc. The surface height, relative surface height, and absolute surface height may be used interchangeable herein.

The surface height at each position of the sample 110 may be measured and used to characterize one or more parameters of the sample 110, including detection of defects, warp, bow, large scale or micro-scale 3D surface topology, or other such characteristics, using measurements from a reference sample, as discussed herein. The reference measurements may be obtained from the same metrology device 100 or a different metrology device, and may be stored in a permanent or semi-permanent memory device. The reference measurements may be imported from on-board memory or from an external memory system. Moreover, the computer system 150 may send data to other systems via a transmission medium. For example, the surface topography of the sample 110, or characters of the sample 110, including the presence of one or more defects, including the size, position, type, etc., may be determined by the computer system 150 and may be communicated and stored in an external memory. In another example, the surface topography of the sample 110, or characteristics of the sample 110, including the presence of one or more defects, including the size, position, type, etc., determined by computer system 150 may be communicated to a process tool that causes the process tool to adjust one or more process parameters associated with a fabrication process step of a semiconductor wafer fabrication sequence, e.g., of the sample 110 in a feed forward process, or subsequently processed samples in a feedback process, based on the measured surface topography or characteristics of the sample 110.

The computer system 150 may have sufficient storage or memory to store reference measurements for an entire wafer, e.g., of a reference wafer, or a portion thereof, e.g., pixels from a full scanner field, as opposed to the full wafer. The storage requirements (for a given recipe, for 1× device on 1× layer in the process flow) are linked to the number of pixels for a given Device/Scanner-Field and the number of pixels depends on the optical-magnification used for the inspection (i.e., pixel size at the wafer level). For example, a pixel may be ~1 um×1 um, and accordingly a ~30 mm×30 mm Scanner Field/Shot results in approximately 900 megapixels (30,000×30,000). Storage of pixels with 12-bit values, thus may require 1.4 GB of memory for each Scanner Field/Shot. Of course, if desired, smaller sized pixels, e.g., for higher magnification, or increased size of the Scanner Field/Shot, may be used which will result in corresponding increases in the storage requirements.

The measurement from each position (pixel) from the sample 110 may use data from a corresponding position (pixel) from a reference wafer, as described herein, the stage 122 is configured to precisely and accurately position sample 110. By way of example, stage 122 may be configured to repeatedly position the sample 110 at desired positions with high precision. In order to use data from corresponding positions (pixels) from a reference wafer, as described herein, the positioning accuracy (XY placement) of the stage 122 should be much less than the size of a pixel in XY dimensions. By way of example, the stage 122 may be configured to repeatedly position the sample 110 at desired positions to +/−10% of a pixel size between two pixels in each of the XY dimensions. Alternative precision, e.g., +/−20%, +/−30%, +/−40%, or +/−50% may be used, but the accuracy of the resulting measurement may suffer accordingly. With +/−10% of a pixel size, i.e., 90% of a pixel is filled with the same underlying pattern from a corresponding pixel on the reference wafer, the comparison of pairs of pixels is valid. On the other hand, if there is >100% of a pixel XY positioning accuracy between positions, the field of view may be more than a whole pixel off, i.e., 0% a pixel is filled with the same underlying pattern from a corresponding pixel on the reference wafer, and thus, the comparison of pixels may not be valid. If desired, an accuracy greater than +/−10% of a pixel size may be used, but there may be diminishing returns due to noise and cost inflation. It should be noted that the process described herein may be used with any pixel size, and the storage requirements, and precision of the stage 122 will scale accordingly.

Figure 3A:
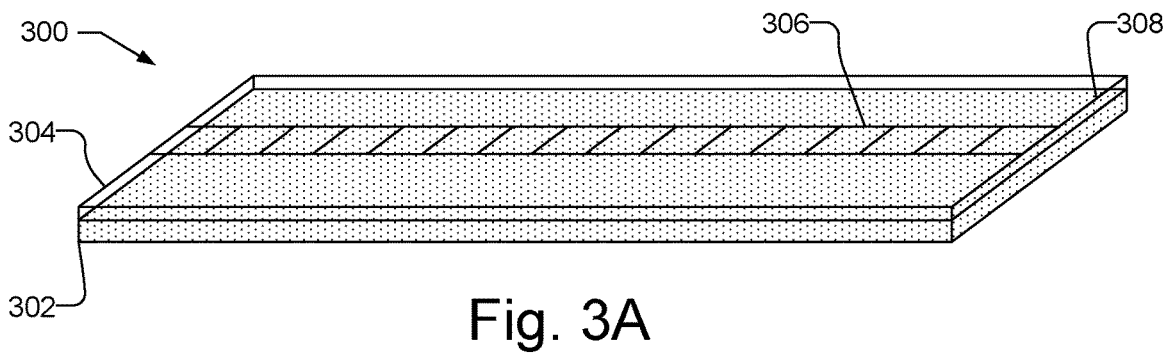
FIGS. 3A and 3B respectively illustrate a portion of an unpatterned sample with an at least partially transparent surface layer and a graph illustrating an interferometer (I.F.) signal corresponds to the measured height at a plurality of positions on the unpatterned sample.
Figure 3B:
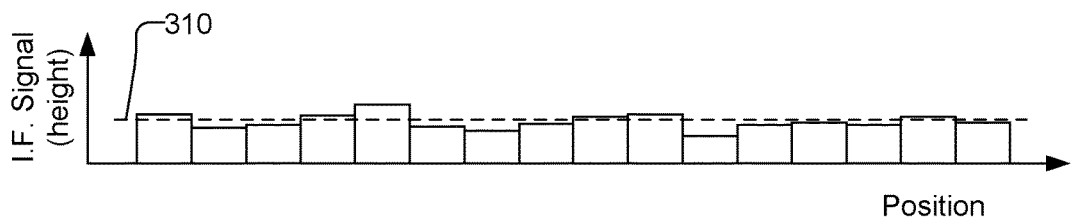

FIG. 3A illustrates a portion of an unpatterned sample 300, which may include a substrate 302 and an overlying surface layer 304. There may be one or more unpatterned layers below the surface layer 304. The surface layer 304 may be at least partially transparent to the wavelengths of light used by the optical metrology device to be used to measure the surface topology of the sample 300, which may be, e.g., optical metrology device 100 shown in FIGS. 1 and 2. For example, the surface layer 304 may be Silicon Oxide, e.g., glass, or any other film that is at least partially transparent to the operable wavelengths of light, and the wavelengths of light used by the optical metrology device may be, e.g., infrared, or Deep UV or Visible light, e.g., X=240 nm to 800 nm. FIG. 3A illustrates a plurality of measurement positions, referred to herein as pixels 306, at which a surface height is to be measured by the optical metrology device. It should be understood that the pixels 306 are not physical patterns on the sample 300, but illustrate positions on the sample 300 for which the optical metrology device measures a height of the top surface 308 of the sample 300. FIG. 3B is a graph illustrating an interferometer (I.F.) signal, which corresponds to the height, e.g., the relative height, for each pixel 306 in FIG. 3A. For illustration, the height bars in the graph of FIG. 3B are aligned with corresponding pixels in FIG. 3A. The dotted line 310 in FIG. 3B illustrates, e.g., an average height of the pixels 306. While the surface layer 304 is at least partially transparent to the wavelengths of light used by the optical metrology device, the sample 300 is unpatterned, i.e., the layers under surface layer 304 are unpatterned and, accordingly, the measured I.F. signal will correspond well to the relative height of the top surface 308 of the sample 300. The I.F. signal correlation to the topography of the top surface 308 improves when there is less topographical variation in the surface of substrate 302 relative to the topographical variation of top surface 308. The I.F. signal correlation to the topography of the top surface 308 also improves the less reflective that the surface of substrate 302 is relative to the top surface 308.

Figure 4A:
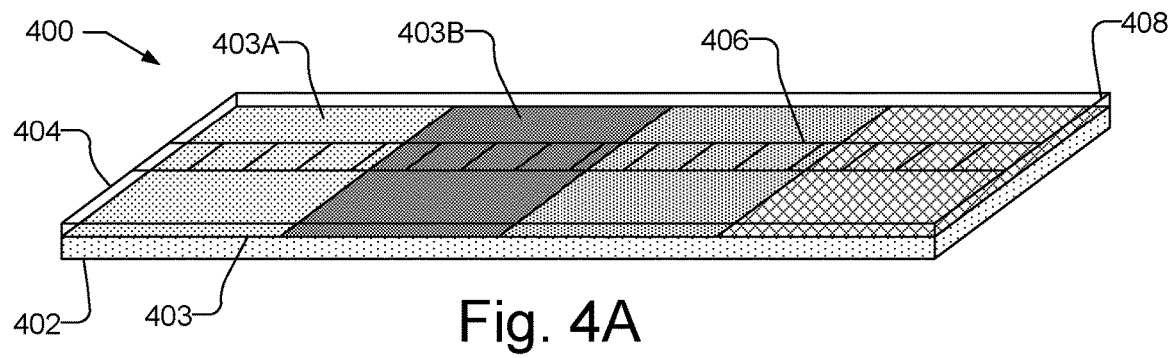
FIGS. 4A and 4B respectively illustrate a portion of a patterned sample with an at least partially transparent surface layer and a graph illustrating an interferometer (I.F.) signal corresponds to the measured height at a plurality of positions on the patterned sample.
Figure 4B:
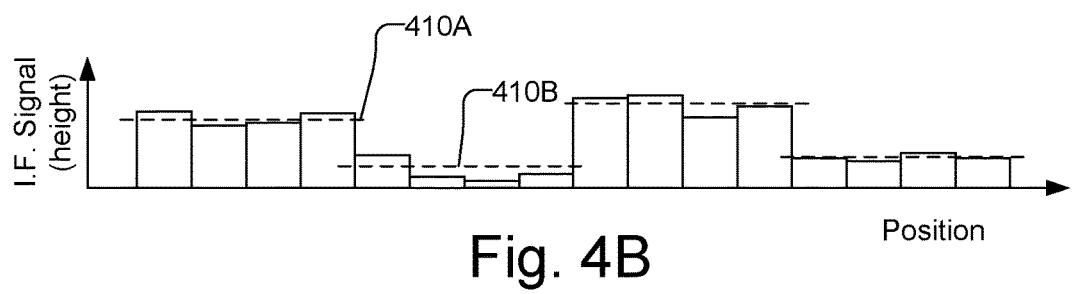

FIGS. 4A and 4B are similar to FIGS. 3A and 3B, but illustrate a patterned sample 400 and an example of the measured interferometer (I.F.) signal that may result from a patterned sample. The patterned sample 400 includes a substrate 402 with one or more patterned layers 403 over the substrate 402 and an overlying surface layer 404. As illustrated by different shadings on layer 403, the pattern of the layer 403 changes based on position. Similar to sample 300 in FIG. 3A, the surface layer 404 may be at least partially transparent to the wavelengths of light used by the optical metrology device, e.g., optical metrology device 100 shown in FIGS. 1 and 2. FIG. 4B is a graph of the interferometer (I.F.) signal, illustrating a height bar aligned with each overlying pixel 406 in FIG. 4A. Because the surface layer 404 is partially transparent to the wavelengths of light used to measure the surface height, the pattern underlying the surface layer 404 may affect the resulting height measurements. The patterns underlying surface layer 404 at regions 403A and 403B may contribute more to the I.F. signal variation than the surface topography of the surface layer 404. In other words, the resulting I.F. signal does not correspond well to the relative height of the top surface 408 of the patterned sample 400. For example, the difference between dotted lines 410A and 410B in FIG. 4B illustrates relative differences between the average height of pixels 408 over different patterned regions. The differences between the I.F. signal at different pixels may be dominated by effects arising between the underlying pattern and the illuminating light when pattern features are smaller than the wavelength of light. Thus, the relative differences in the "reported Z-height" from the I.F. signal does not correspond to the actual surface height of the sample.

Figure 5A:
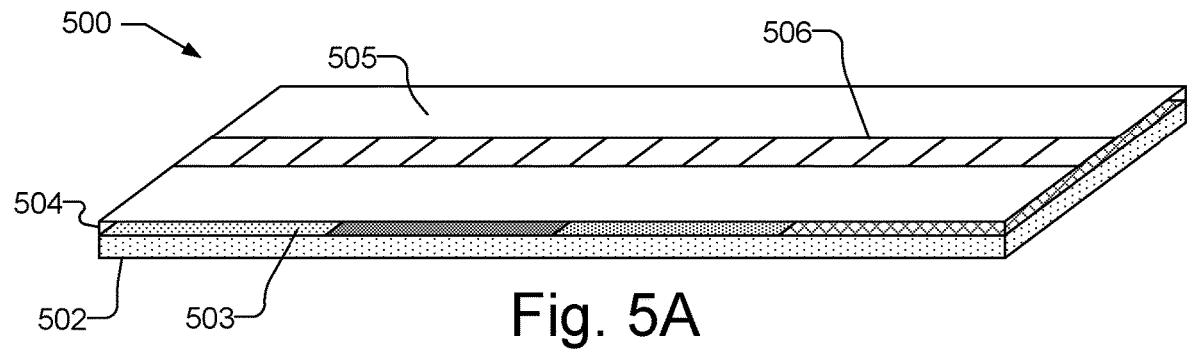
FIGS. 5A and 5B respectively illustrate a portion of a patterned sample with an at least partially transparent surface layer covered with a thin opaque film and a graph illustrating an interferometer (I.F.) signal corresponds to the measured height at a plurality of positions on the patterned sample.
Figure 5B:
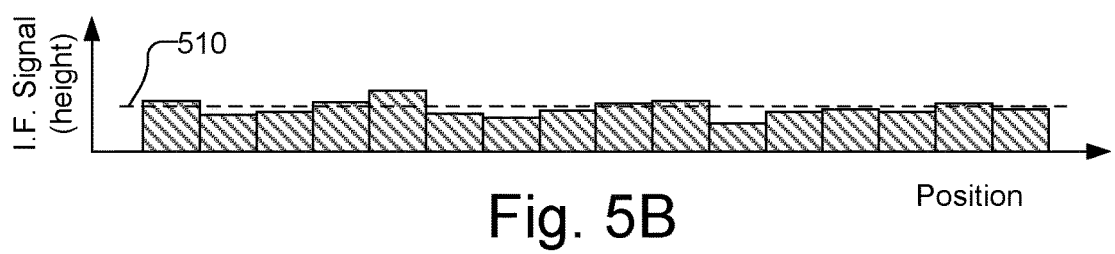

FIG. 5A is similar to FIG. 4A, but illustrates a patterned sample 500, which is similar to patterned sample 400, with a substrate 502, patterned layers 503, and an at least partially transparent layer 504, but includes a thin, reflective, opaque layer 505 overlying the layer 504. The opaque layer 505 over surface layer 404 is non-transparent to the wavelengths of light used by the optical metrology device to measure the surface topography of the sample 500. For example, the opaque layer may be a thin Titanium Nitride film or other material that is not transparent to the operable wavelengths of light, and may be, e.g., via Chemical Vapor Deposition (CVD), Plasma Vapor Deposition (PVD), or Atomic Layer Deposition (ALD), or any other appropriate manner. FIG. 5B is a graph illustrating the interferometer (I.F.) signal for each pixel 506 in FIG. 5A that is aligned above a corresponding height bar in FIG. 5B, where dotted line 510 illustrates, e.g., an average height of the pixels 506. Because the opaque film 505 is non-transparent to the illuminating light, the effects arising between the underlying pattern on layer 503 and the illuminating light are blocked by the opaque film 505. Accordingly, the relative differences in the "reported Z-height" from the I.F. signal at different pixels corresponds well to the actual surface topography of the sample 500 regardless of underlying patterns. Unfortunately, while the use of the opaque film 505 provides an accurate surface topography measurement, i.e., relative surface height at multiple positions regardless of underlying patterns, if the opaque film 505 is not a standard part of the manufacturing process flow, adding the opaque film 505 to the sample 500 for metrology is destructive, resulting in chips that will not function.

Figure 6A:
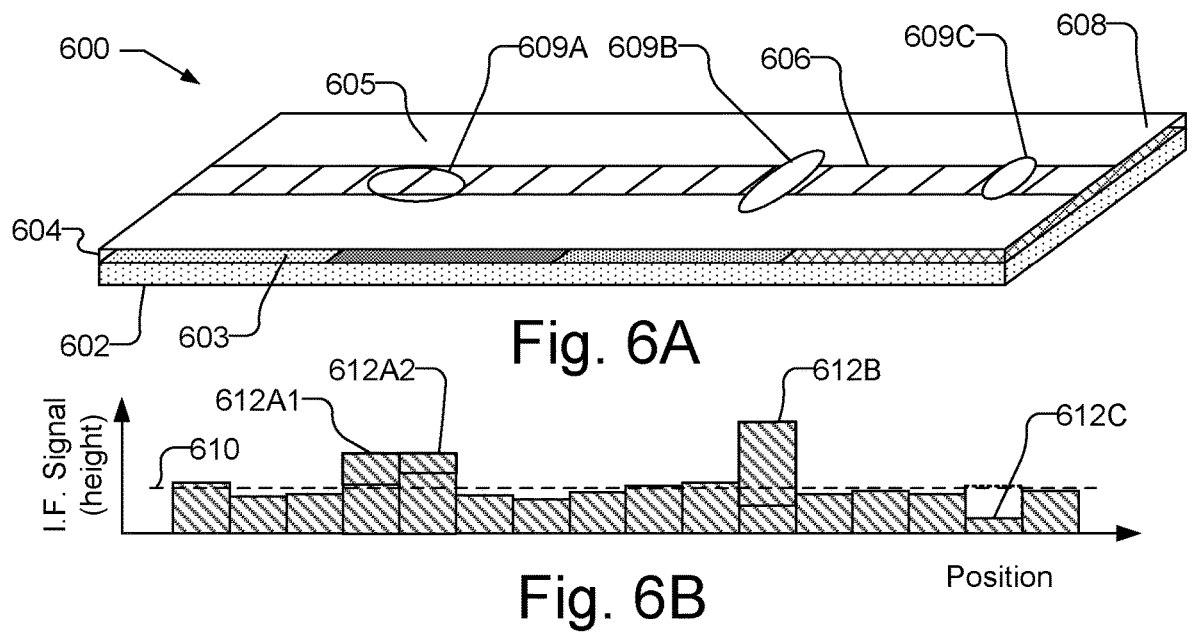
FIGS. 6A and 6B respectively illustrate a portion of a patterned sample with an at least partially transparent surface layer covered with a thin opaque film and having defects and a graph illustrating an interferometer (I.F.) signal corresponds to the measured height at a plurality of positions on the patterned sample.
Figure 6B:
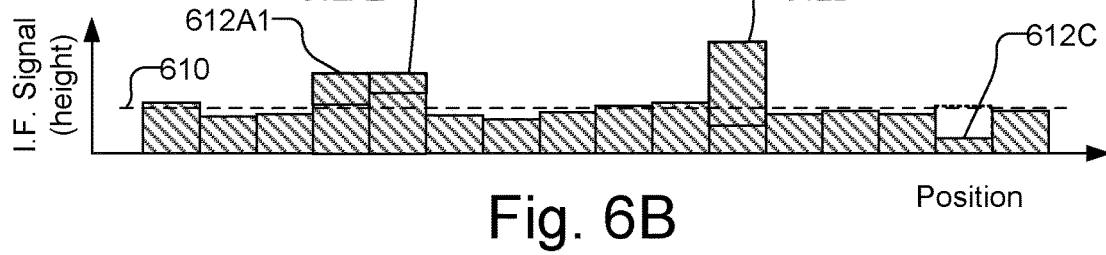

FIG. 6A is similar to FIG. 5A, but illustrates a patterned sample 600, which is similar to patterned sample 500, with a substrate 602, patterned layers 603, an at least partially transparent layer 604 and an overlying opaque layer 605, but further illustrates defects in the form of bumps 609A and 609B, which extend above the top surface 608 of the sample 600 and a dip 609C, which extends below the top surface 608 of the sample 600. FIG. 6B is a graph illustrating the interferometer (I.F.) signal for each pixel 606 in FIG. 6A that is aligned above a corresponding height bar in FIG. 6B. As illustrated by height bars 612A1, 612A2, 612B, and 612C in FIG. 6B, the bumps 609A and 609B and dip 609C clearly stand out with respect to the average height, illustrated by dotted line 610, irrespective of the presence of any underlying patterned film 603.

Figure 7A:
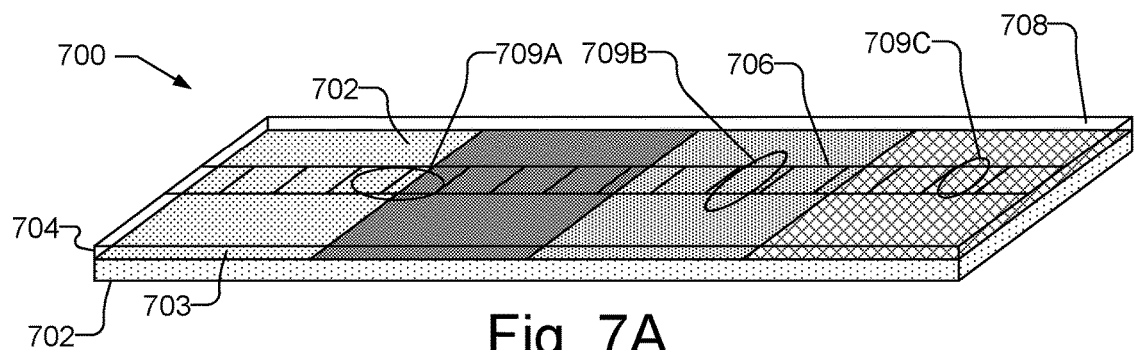
FIGS. 7A and 7B respectively illustrate a portion of a patterned sample with an at least partially transparent surface layer having defects and a graph illustrating an interferometer (I.F.) signal corresponds to the measured height at a plurality of positions on the patterned sample.
Figure 7B:
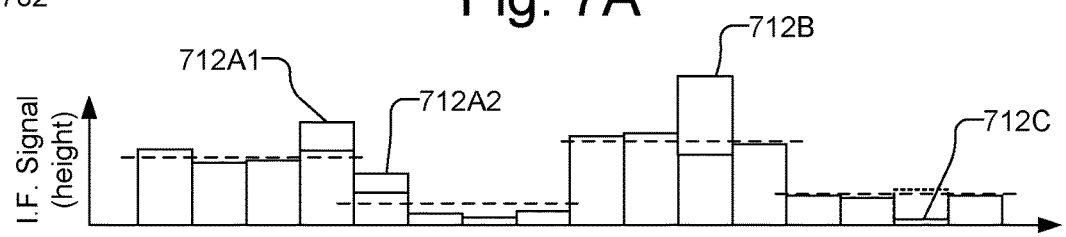

FIG. 7A is similar to FIGS. 4A and 6A, but illustrates a patterned sample 700, which is similar to patterned sample 400, with a substrate 702, patterned layers 703, an at least partially transparent layer 704 (and does not include an overlying opaque film) and includes defects in the form of bumps 709A and 709B, which extend above the top surface 708 of the sample 700 and a dip 709C, which extends below the top surface 708 of the sample 700. FIG. 7B is a graph illustrating the interferometer (I.F.) signal from the optical metrology device for each pixel 706 in FIG. 7A that is aligned above a corresponding height bar in FIG. 7B. As illustrated by height bars 712A1, 712A2, 712B and 712C in FIG. 7B, the I.F. signal variation caused by defects may be lower in magnitude than the I.F. signal variation caused by effects arising between the underlying patterns and the illuminating light. For example, the relative differences in "reported Z-height" from the I.F. signal illustrated at bars 712A1 and 712A2 is dominated by effects arising between the underlying patterns and the illuminating light, as opposed to the variation in topography caused by the defect 709A.

Figure 8A:
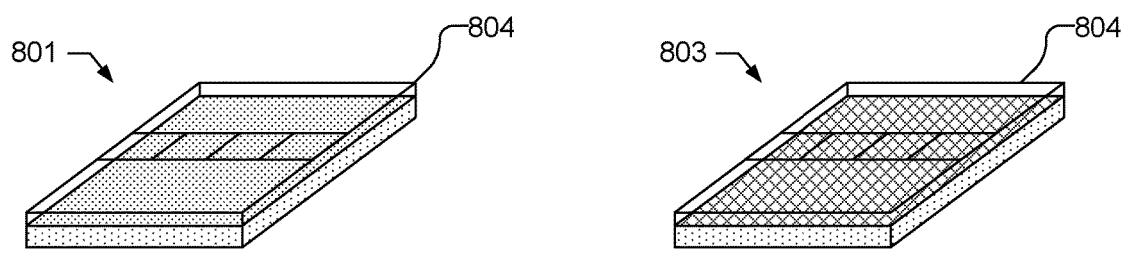
FIGS. 8A and 8B respectively illustrate differently patterned portions of a patterned sample with an at least partially transparent surface layer having defects and graphs illustrating interferometer (I.F.) signals corresponding to measured height differences within each portion of the patterned sample.
Figure 8B:

FIG. 8A illustrate different portions 801 and 803 of a patterned sample, which include an at least partially transparent surface layer 804 and differently patterned layers underlying surface layer 7804. FIG. 8B illustrates graphs illustrating interferometer (I.F.) signals for each pixel in each of the portions 801 and 803 illustrated in FIG. 8A. As illustrated, a comparison of the signals (relative heights) from identically patterned positions, e.g., a comparison between the signals from the pixels on portion 801 or a comparison between the signals from the pixels on portion 803, produces a height differential Δ that is strongly correlated to the differences in the actual surface heights at those pixels. However, as shown in FIG. 4B, a comparison of signals from pixels with different underlying patterns would result in a height differential that does not correspond well to the difference in the actual surface heights at those pixels because the underlying patterns may contribute more to the I.F. signal variation than the surface topography.

Figure 9:
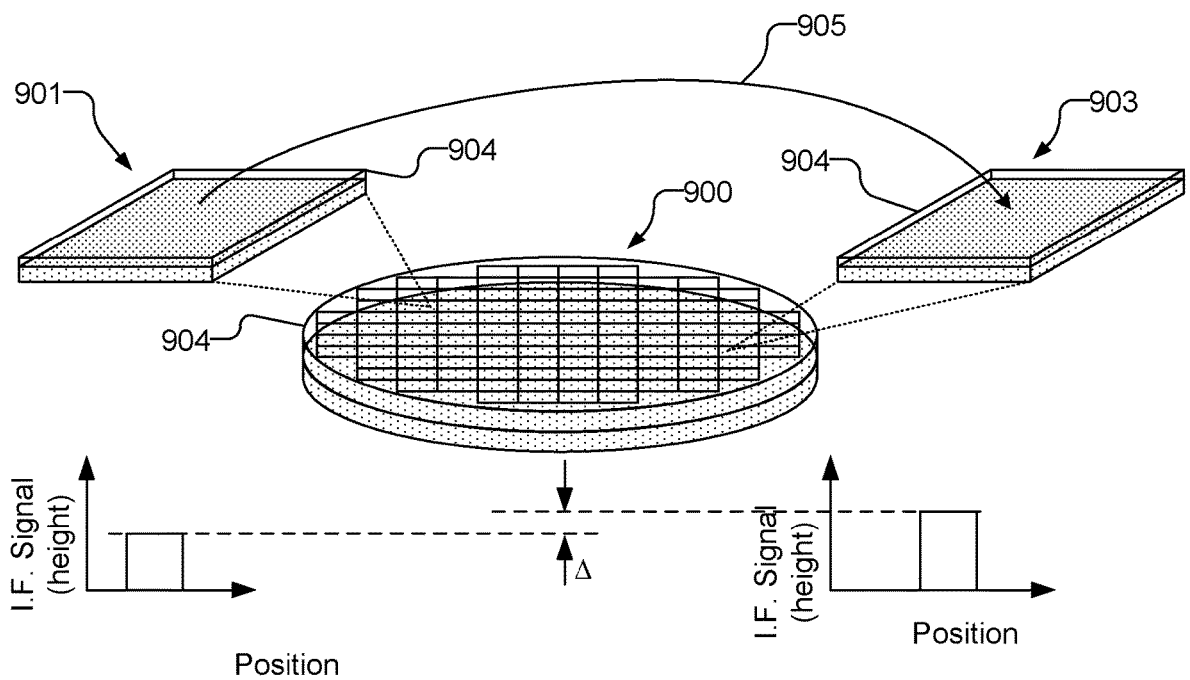
FIG. 9 illustrates a patterned wafer with an at least partially transparent surface layer and measured height differences between positions on the patterned wafer that have the same underlying pattern.

FIG. 9 illustrates a patterned wafer 900 that includes an at least partially transparent surface layer 904. When determining the surface topography of the patterned wafer 900 based on a relative difference between pixels, the pixels used for comparison may be from different die (or the same die) if the pixels have the same underlying pattern. For example, FIG. 9 illustrates with arrow 905 that a first pixel 901 from a first die on the patterned wafer 900 is compared to a second pixel 903 from a different die on the patterned wafer 900, which have the same underlying pattern. The first pixel 901 and second pixel 903, for example, may have the same within-die coordinates, i.e., the same (X,Y) position within their respective die, or may be from different within-die positions (within the same die or different die) but are known to have the same underlying pattern, e.g., from the GDSII file. Because the first pixel 901 and second pixel 903 have the same underlying pattern, the height differential Δ between the IF signals from the pixels is strongly correlated to the actual height difference at those pixels.

While the relative surface heights of pixels on the patterned wafer 900 may be measured and compared to pixels from different positions on the same patterned wafer 900 (or a reference wafer) that have the same underlying patterns, pixels that have different underlying patterns cannot be reliably compared to each other to determine the surface topography because the differing underlying patterns may contribute more to the I.F. signal variation than the surface topography. Accordingly, pixels that may be neighboring, e.g., adjacent or within a single frame of view of a metrology or processing device, may not be compared to determine the surface topography if the pixels have different underlying patterns. As illustrated e.g., in FIGS. 5A and 5B, an opaque film may be deposited over the top surface of the wafer 900 in order to measure the surface topography from pixels with different underlying patterns. The deposition of the opaque film, however, if not part of the manufacturing process flow is a destructive step resulting in non-functioning chips. Accordingly, an opaque film cannot be used for in-process metrology of the surface topography. While this destructive measurement process may be used, e.g., with one sacrificial wafer, to obtain a rough indication of the surface topography from other wafers in process at the same time in the factor, the measurements will not be accurate and wafer-to-wafer or lot-to-lot surface topography variations will not be identified.

According to one aspect, the surface topography of a test sample that has at least a partially transparent surface layer may be accurately measured using a reference wafer that is nominally the same as the test sample. The surface topography of the reference wafer, which also has an at least partially transparent surface layer, may be measured before and after the deposition of a thin, reflective, opaque film over the at least partially transparent top layer. The surface topography measurements are made at the same pixels, i.e., same positions on the wafer, before and after deposition of the opaque film. The surface topography of a test sample, which includes the at least partially transparent top layer but does not have an overlying opaque film, may be measured at the same pixels. A difference between the measured surface heights at corresponding pixels from the reference wafer before deposition of the opaque film and the test sample provides a relative height difference at corresponding pixels. Because the corresponding pixels have the same underlying patterns, the height differential Δ is strongly correlated to the actual height differences at these pixels, but is not strongly correlated to the actual surface height at those pixels, because the pattern underlying the surface layer may contribute more to the I.F. signal than the surface height of the surface layer. The surface height at each pixel of the reference sample is known, however, from the measurement of the pixels on the reference wafer after deposition of the opaque film. Accordingly, the height difference at each pixel may be combined with the relative height measured at each pixel on the reference wafer after deposition of the opaque film to determine the surface height at each pixel on the test sample. The surface height at each pixel on the test sample may be used to characterize the test sample and/or detect defects, which may be used to modify, alter, or inform further processing of the test sample or the processing of subsequently processed samples, e.g., in a feed forward or feedback process. Moreover, because corresponding pixels with the same underlying patterns are used in the present process, the surface topology measurement may be provided for "in-die" positions, and thus, there is no need for scribe-lane structures, which often have a surface topology that varies significantly with respect to in-die positions.

Figure 10:
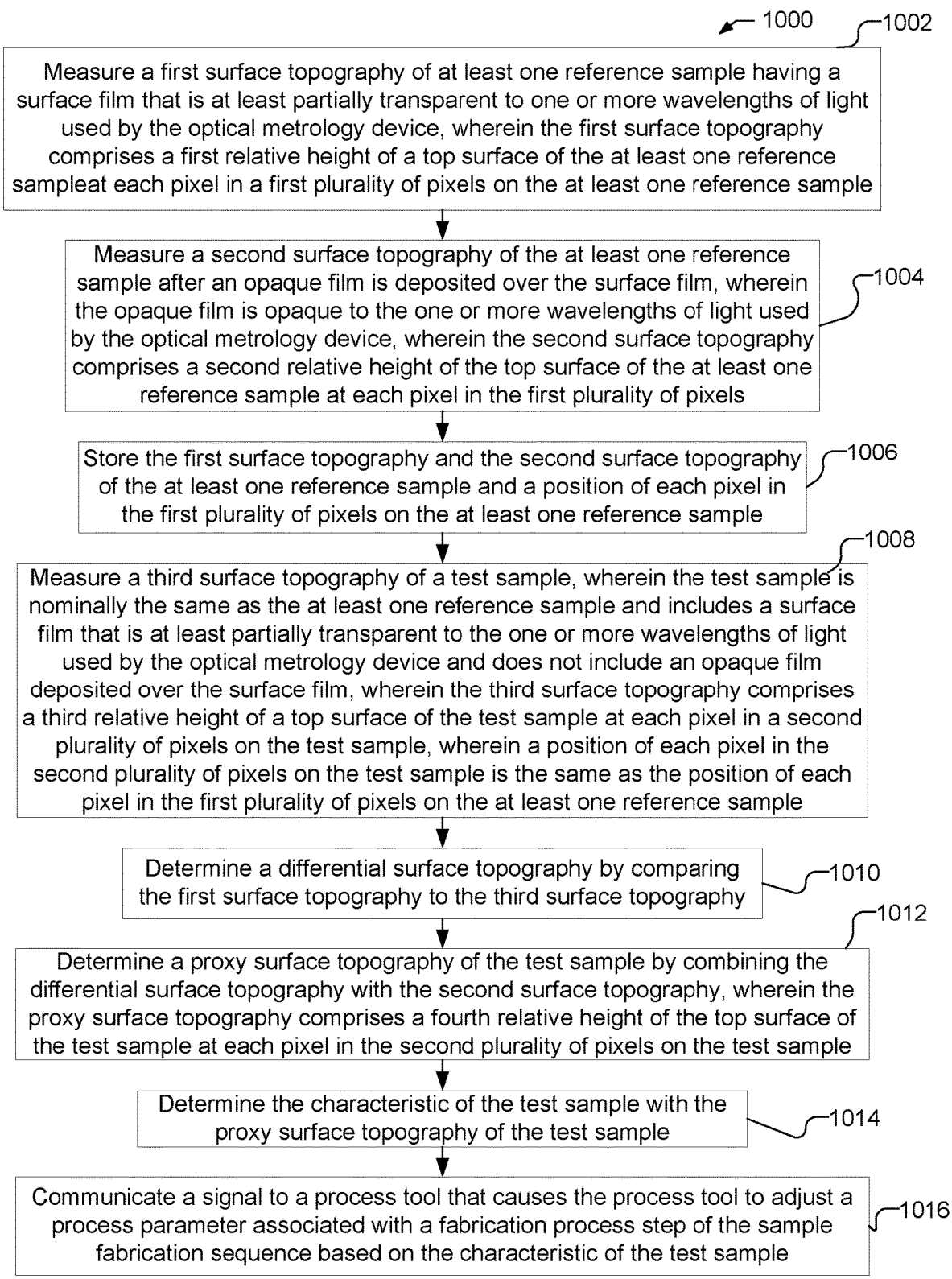
FIG. 10 illustrates a process flow to measure a surface topography of a test sample.

FIG. 10, by way of example, illustrates a process flow 1000 to measure the surface topography of a test sample, e.g., to characterize the test sample using an optical metrology device, such as optical metrology device 100, shown in FIGS. 1 and 2, or other similar metrology devices. As illustrated, an optical metrology device measures a first surface topography of at least one reference sample having a surface film that is at least partially transparent to one or more wavelengths of light used by the optical metrology device (1002). The first surface topography comprises a first relative height of a top surface of the at least one reference sample at each pixel in a first plurality of pixels on the at least one reference sample. It should be understood that the one reference sample or more than one reference sample may be used to produce the first surface topography and the second surface topography. For example, the surface topographies from multiple reference wafers, before and after deposition of the opaque film, may be measured and statistically combined, e.g., as an average, weighted average, mean, median, mode, etc., to produce the first surface topography and the second surface topography.

Figure 11:
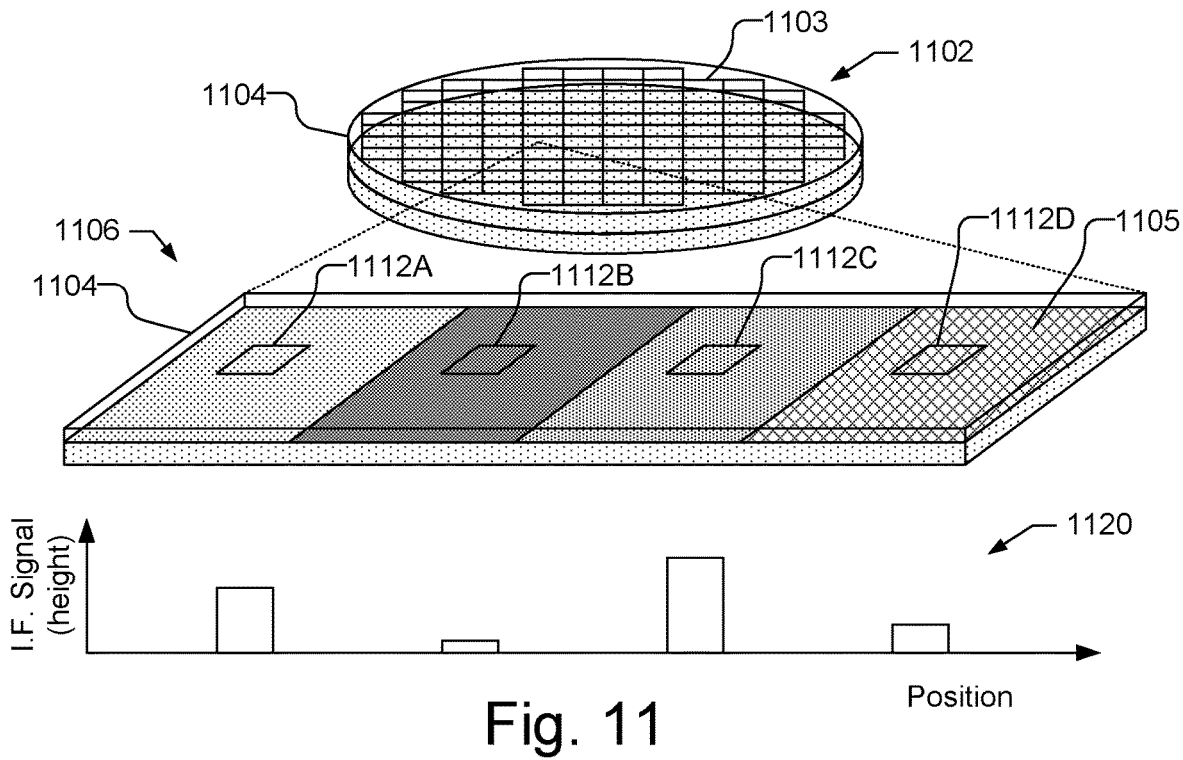
FIG. 11 illustrates a reference sample with an at least partially transparent surface layer and a measured surface topography.

FIG. 11, by way of illustration, shows a reference sample 1102, which may be, e.g., a semiconductor wafer with a plurality of dies 1103 in process. The reference sample 1102 includes a surface film 1104 that is at least partially transparent to one or more wavelengths of light used by the optical metrology device, such as that shown in FIGS. 1 and 2. For example, the surface film 1104 may be Silicon Oxide (SiO$_2$), and visible wavelengths of light in the range 400 nm to 800 nm may be used by the metrology device. As illustrated, by the enlarged portion 1106 of the reference sample 1102 and the underlying graph, which illustrates an interferometer (I.F.) signal indicating relative height for each position, a first surface topography 1120 of the reference sample 1102 is measured to obtain first relative heights of the top surface 1105 of the reference sample 1102 at each pixel 1112A, 1112B, 1112C, and 1112D in a first plurality of pixels, collectively referred to sometimes as pixels 1112. As illustrated, there may be different patterns underlying the surface film 1104, which may contribute more to the I.F. signal variation than the height of the top surface 1105 of the surface film 1104. It should be understood that while enlarged portion 1106 illustrates only four pixels 1112 from a single die, the plurality of pixels 1112 may include many more pixels within the same die and from multiple dies on the reference sample 1102.

Referring back to FIG. 10, the optical metrology device measures a second surface topography of the at least one reference sample after an opaque film is deposited over the surface film, wherein the opaque film is opaque to the one or more wavelengths of light used by the optical metrology device (1004). The second surface topography comprises a second relative height of the top surface of the at least one reference sample at each pixel in the first plurality of pixels.

Figure 12:
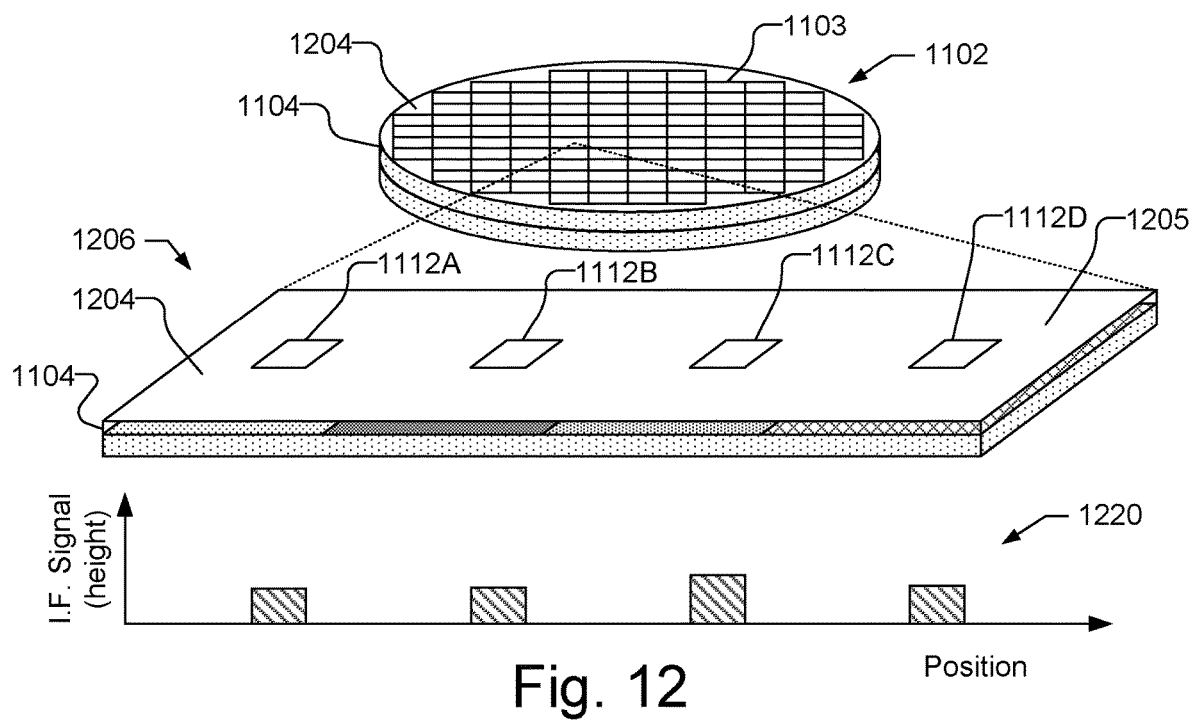
FIG. 12 illustrates the reference sample from FIG. 11 with a thin opaque film overlying the at least partially transparent surface layer and a measured surface topography.

FIG. 12 shows, by way of illustration, the reference sample 1102 from FIG. 11 after an opaque film 1204 has been deposited over the surface film 1104. The opaque film 1204 may be a thin film so that it is conformal, but still opaque (or minimally-transparent film) that is deposited in a way that does not change the relative Z-heights of different XY coordinates before and after film deposition. The opaque film 1204, for example, may have a thickness of 30 nm, and may be, e.g., Tungsten, Tantalum Nitride, or Copper, all three of which have a transparency of less than 20% for blue light at normal incidence when the thickness of the film is 30 nm. With this example, and assuming the surface film 1104 is 100% reflective, approximately 4% of the incident light will be returned, i.e., 20% of the light will be transmitted through to the opaque film 1204 and 20% will be reflected back to be returned to the detector (20%×20%=4%). Thus, the combined thickness and transparency of the opaque film 1204 should be such that no or little reflected light is returned from the underlying patterns on the sample. By way of example, the opaque film 1204 may permit less than 20% of the incident light to be returned from the underlying patterns. In some implementations, the opaque film 1204 may permit less than 10%, or 5%, or 1% of the incident light to be returned from the underlying patterns. If desired, the opaque film 1204 may be thicker, and a more transparent material may be used, if the extra thickness is of consistent depth across the sample, e.g., the opaque film 1204 is deposited in a way that does not significantly change the relative Z heights of different XY coordinates within a pixel. By way of example, the opaque film 1204 may be a film of Titanium Nitride that is approximately 100 nm or more thick. The opaque film 1204 ideally is a conformal film so that it has a thickness is the same across the surface of the reference sample 1102. While the opaque film 1204 increases the surface height of the top surface 1205 of the reference sample 1102, the opaque film 1204 is uniformly deposited, e.g., so that it is conformal, and the relative surface height of the top surface 1205 is not altered significantly, e.g., any variation in the change in relative surface height will not alter the resulting measurements greater than expected noise. Moreover, if an absolute surface height of the top surface of the reference sample 1102 is desired, e.g., a height relative to another object such as the top surface of the chuck 120 (shown in FIG. 1), the thickness of the opaque film 1204 may be subtracted from the absolute surface height measurement. As illustrated by the enlarged portion 1206 of the reference sample 1102 and the underlying graph, which illustrates an interferometer (I.F.) signal indicating relative height for each position, a second surface topography 1220 of the reference sample 1102 is measured to obtain second relative heights of the top surface 1205 of the reference sample 1102 at each pixel 1112A, 1112B, 1112C, and 1112D in the first plurality of pixels 1112. While there may be different patterns underlying the surface film 1104, the effects arising between the underlying pattern and the illuminating light are blocked by the opaque film 1204 and thus, the measured relative heights of the pixels in the second surface topography measurement correspond well to the actual surface topography of the reference sample 1102.

It should be noted that the second surface topography 1220 is measured at the same pixels 1112 as the first surface topography 1120, but after the opaque film 1204 has been deposited. Thus, after the measurement of the first surface topography 1120, the reference sample 1102 is unloaded from the optical metrology device, processed to deposit the opaque film 1204 and again loaded onto the optical metrology device. The optical metrology device, e.g., stage 122 in FIG. 1, ideally positions the reference sample 1102 to measure the second surface topography at the precisely the same positions used to measure the first surface topography, but some variation in position may be acceptable, e.g., +/−10% of a pixel size in each of the XY dimensions. Reduced precision in positioning, e.g., +/−20%, +/−30%, +/−40%, or +/−50% of the pixel size, may also be acceptable, but the accuracy of the resulting measurement may suffer accordingly.

Referring back to FIG. 10, the first surface topography and the second surface topography of the at least one reference sample are stored along with a position of each pixel in the first plurality of pixels on the at least one reference sample (1006). For example, the first surface topography and the second surface topography and positions associated with each pixel may be stored in memory 154 and/or storage 156 of computer system 150 shown in FIG. 1.

Figure 13:
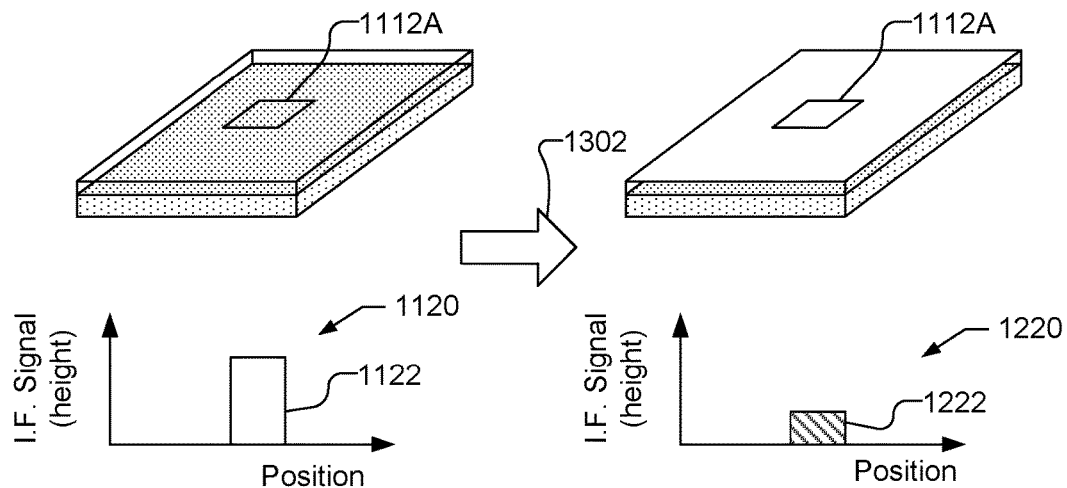
FIG. 13 illustrates an association of the position and relative heights of positions on the reference sample of FIGS. 11 and 12 to be stored in memory.

FIG. 13, by way of example, illustrates with arrow 1302 an association of the position and relative heights 1122 and 1222 for pixel 1112A from the first surface topography 1120 and the second surface topography 1220 of the reference sample 1102, e.g., before and after deposition of the opaque film 1204, which is stored in memory of the metrology device. While FIG. 13 illustrates a single pixel 1112A, the position and relative heights, before and after deposition of the opaque film 1204, for each pixel in the plurality of pixels 1112 may be stored.

Referring back to FIG. 10, the optical metrology device measures a third surface topography of a test sample, wherein the test sample is nominally the same as the at least one reference sample and includes a surface film that is at least partially transparent to the one or more wavelengths of light used by the optical metrology device and does not include an opaque film deposited over the surface film (1008). The third surface topography comprises a third relative height of a top surface of the test sample at each pixel in a second plurality of pixels on the test sample, wherein a position of each pixel in the second plurality of pixels on the test sample is the same as the position of each pixel in the first plurality of pixels on the at least one reference sample.

Figure 14:
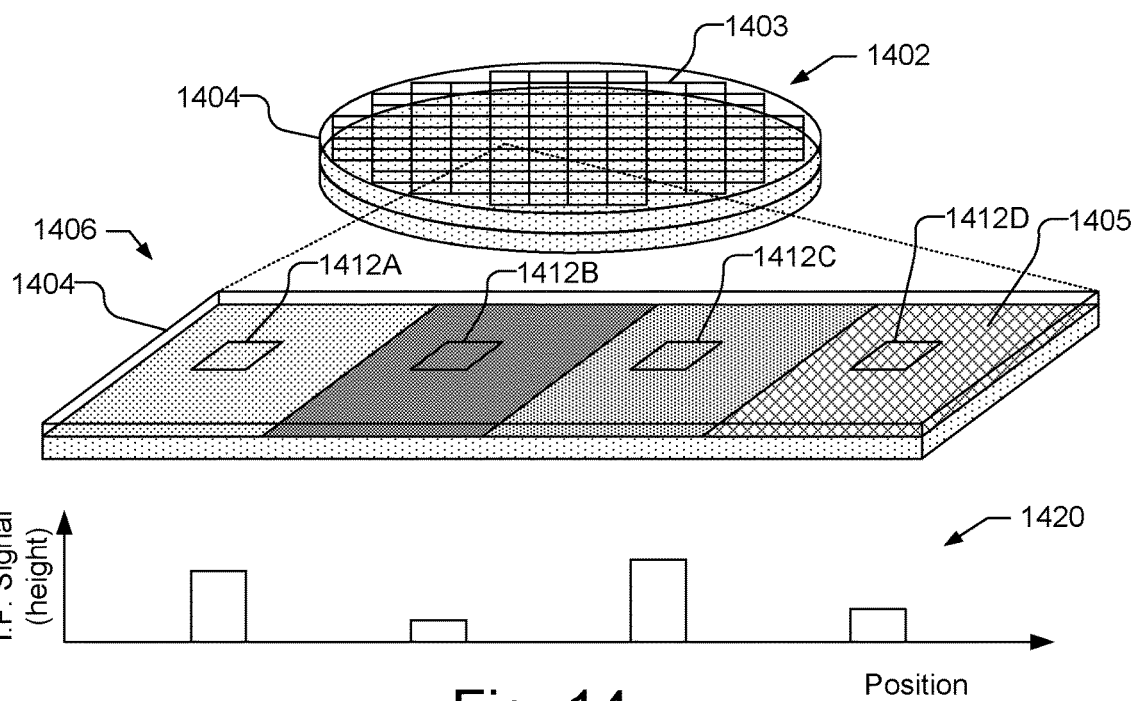
FIG. 14 illustrates a test sample with an at least partially transparent surface layer and a measured surface topography.

FIG. 14, by way of illustration, shows a test sample 1402, which is nominally the same as the reference sample 1102. The test sample 1402, for example, is a semiconductor wafer with a plurality of dies 1403 in process and is at the same processing step as reference sample 1102. Thus, test sample 1402 includes the same surface film 1404 as surface film 1204 on reference sample 1102, which is at least partially transparent to the one or more wavelengths of light used by the optical metrology device. The test sample 1402, however, does not include an opaque film deposited over the surface film. As illustrated, by the enlarged portion 1406 of the reference sample 1402 and the underlying graph, which illustrates an interferometer (I.F.) signal indicating relative height relative to position, a third surface topography 1420 of the test sample 1402 is measured to obtain first relative heights of the top surface 1405 of the test sample 1402 at each pixel 1412A, 1412B, 1412C, and 1412D in a second plurality of pixels, collectively referred to sometimes as pixels 1412. As the test sample 1402 is nominally the same as the reference sample 1102, the topography 1420 of the test sample 1402 will likely be similar to, but different than, the topography 1120 measured from the reference sample 1102. The positions of pixels 1412 correspond to the positions of pixels 1112. Thus, the optical metrology device, e.g., stage 122 in FIG. 1, ideally positions the test sample 1402 to measure pixels 1412 at precisely the same positions as pixels 1112 in reference sample 1102, although some variation in positioning may be acceptable, e.g., +/−10% of a pixel size in each of the XY dimensions. Reduced precision in positioning, e.g., +/−20%, +/−30%, +/−40%, or +/−50% of the pixel size, may be acceptable, but the accuracy of the resulting measurement may suffer accordingly.

It should be understood that if desired, the first surface topography and the second surface topography of the reference sample may be measured by a different optical metrology device than used to measure the third surface topography of the test sample. The optical metrology device that measures the third surface topography of the test sample may store and obtain the first and second surface topographies from memory.

Referring back to FIG. 10, a differential surface topography is determined by comparing the first surface topography to the third surface topography (1010). For example, the differential surface topography may be determined as a height difference between the first relative height at each pixel in the first plurality of pixels in the first surface topography and the third relative height at each corresponding pixel in the second plurality of pixels in the third surface topography. Corresponding pixels are pixels that are at the same relative positions on the at least one reference sample and the test sample, e.g., with an acceptable precision such as +/−10%, +/−20%, +/−30%, +/−40%, or +/−50% of the pixel size in each of the XY dimensions.

A proxy surface topography of the test sample is determined by combining the differential surface topography with the second surface topography (1012). The combination, e.g., addition, of the differential surface topography and the second surface topography, in effect, stands in for the use of an opaque film on the test sample to determine the surface height and accordingly is referred to herein as a "proxy surface topography" or "proxy surface height." The proxy surface topography comprises a fourth relative height of the top surface of the test sample at each pixel in the second plurality of pixels on the test sample. For example, the proxy surface topography may be determined by combining the height difference at each pixel in the second plurality of pixels on the test sample and the second relative height at each corresponding pixel in the first plurality of pixels on the at least one reference sample.

The proxy surface topography of the test sample may be used in various manners to characterize the test sample. As illustrated in FIG. 10, the proxy surface topography of the test sample is used to determine the characteristic of the test sample (1014). For example, the proxy surface topography of the test sample may be used to detect defects on the test sample. By way of illustration, the relative height at each pixel in the proxy surface topography may be compared to a predetermined, e.g., user definable, threshold height, e.g., to determine if any pixels are so statistically abnormal in terms of their Z-heights relative to other pixels that the pixels should be considered an aberration or defective, and an indication that the test sample includes a defect is provided if the relative height of any pixel is greater than the predetermined threshold height. Alternatively, the relative height at each pixel in the proxy surface topography may be compared to a Depth of Focus window for a processing tool, wherein an indication that the test sample includes a defect is provided if the relative height of any pixel is outside the Depth of Focus window. The Depth of Focus window, for example, may be range of focus for a processing tool that will permit given features that are being produced to be kept within all specifications, e.g., linewidth, sidewall angle, resist loss, etc., over a specified exposure range. It is noted that the Depth of Focus window monitors a different type of defect than a predetermined threshold height, as many pixels may be outside the Depth of Focus window, e.g., if there were a major misprocess problem, in which case a statistically-abnormal threshold, as used with the predetermined threshold height, may not identify these pixels. In another example, the proxy surface topography of the test sample may be used to characterize the test sample by measuring, e.g., at least one of warp, bow, large scale and/or micro-scale 3D surface topology, or other similar characteristics, including a combination thereof. For example, the relative surface heights of all the pixels may be compared to describe the warp or bow or the large scale or micro-scale 3D surface topology.

As shown in FIG. 10, a signal is communicated to a process tool that causes the process tool to adjust a process parameter associated with a fabrication process step of the sample fabrication sequence based on the characteristic of the test sample (1016). Thus, the characteristic, such as an indication of a defect, or warp, bow, etc., may be used to modify, alter, or inform further processing of the test sample or the processing of subsequently processed samples, e.g., in a feed forward or feedback process. In this regard, measurement results may be exported to another system.

Figure 15:
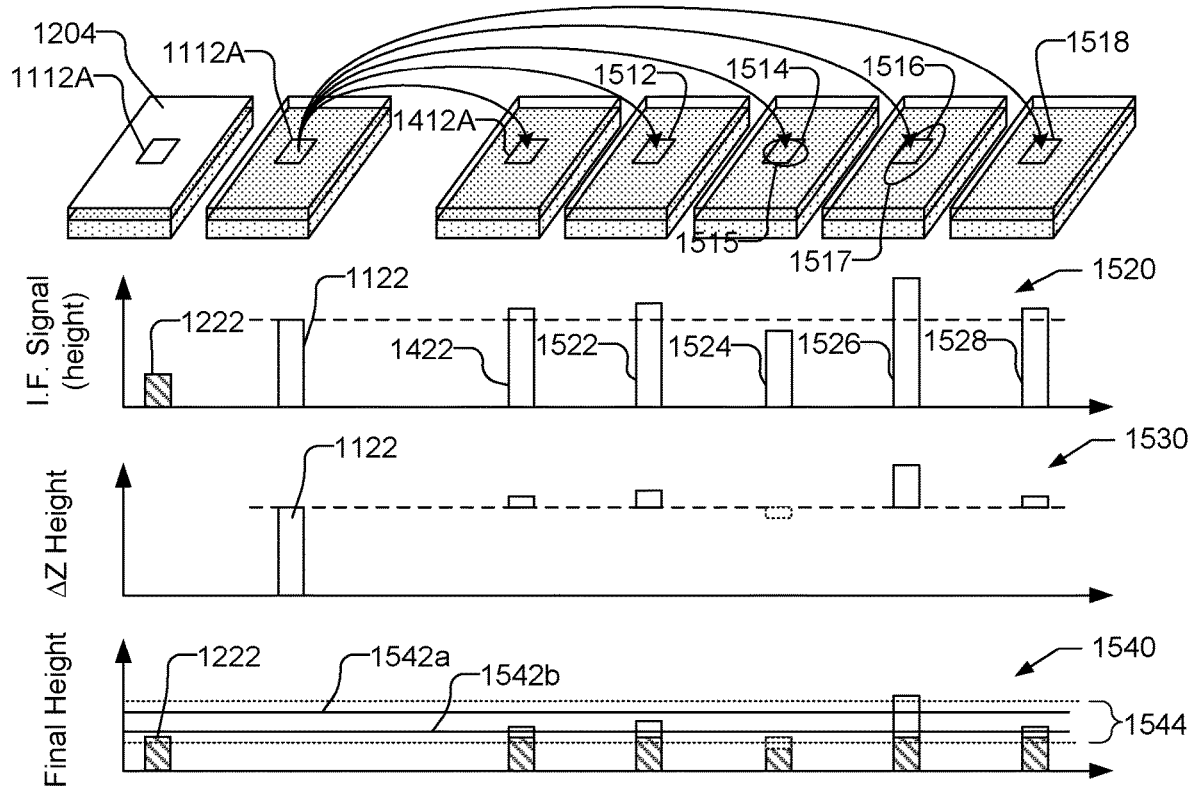
FIG. 15 illustrates corresponding positions on a reference sample, before and after deposition of an opaque film, and multiple test samples, with underlying graphs showing measured relative heights, height differences between the pre-opaque film reference sample and the test sample, and the actual heights of the positions on the test samples as a combination of measured relative heights of the post-opaque film reference sample and the height differences.

FIG. 15, by way of example, illustrates a single pixel 1112A from the reference sample 1102, sometimes referred to herein as a reference pixel 1112A, before and after deposition of the opaque film 1204. Additionally, FIG. 15 illustrates a corresponding pixel 1412A from test sample 1402 shown in FIG. 14, as well as corresponding pixels from four additional test samples, illustrated as pixels 1512, 1514, 1516, and 1518, sometimes referred to herein as test pixels. The corresponding pixels 1112A, 1412A, 1512, 1514, 1516, and 1518, for example, may have the same wafer coordinates, e.g., (X,Y) position on the wafer (within a desired precision). If desired, one or more of the pixels may have different wafer coordinates but may have the same within-die coordinates (and one or more pixels may be from the same test sample or a different test sample). Additionally, if desired, one or more of the corresponding pixels may have different within-die positions (within the same die or different die), but are known to have the same underlying pattern, e.g., from the GDSII file, for example, as found inside a repeating structure, such as a within the array area of a memory chip. Under each pixel, graph 1520 illustrates the relative height measurements for the pixels, including relative height measurements 1122 and 1222 for the pixel 1112A before and after deposition of the opaque film 1204, relative height measurement 1422 for pixel 1412A for test sample 1402, and relative height measurements 1522, 1524, 1526, and 1528 for pixels 1512, 1514, 1516, and 1518, respectively.

FIG. 15 further includes a graph 1530 that illustrates a height difference (ΔZ height) between the reference pixel 1112A and each of the test pixels 1412A, 1512, 1514, 1516, and 1518. It should be understood that FIG. 15 illustrates only a single reference pixel and corresponding test pixel for five different test samples, but that a differential surface topology may be determined for each test sample by comparing the measured surface topography for each test sample (i.e., at a plurality of pixels) to the pre-opaque film measurement of the surface topography of the reference sample (i.e., at corresponding pixels). As can be seen, the relative height of each test pixel is close to the relative height of the reference pixel, except for pixel 1516, which includes a defect 1517.

FIG. 15 further includes a graph 1540 that illustrates a final relative height for each test pixels 1412A, 1512, 1514, 1516, and 1518. The final relative height is determined by combining relative height 1222 from the post-opaque film measurement of the reference pixel 1112A with the height difference for each test pixel shown in graph 1530. It should be understood that the proxy surface topography may be determined for each test sample by combining the differential surface topography for each test sample (i.e., the differential height at a plurality of pixels for each test sample) and the post-opaque film measurement of the surface topography of the reference sample (i.e., at corresponding pixels). Thus, as illustrated, an accurate height measurement at any pixel location of a test sample that has an at least partially transparent film may be obtained without the need to model how the I.F. signal interacts with underlying patterns and films, and without the need of a destructive opaque film.

Moreover, graph 1540 illustrates a predetermined, e.g., a user selectable, threshold heights with thresholds 1542a and 1542b that may be used to indicate the presence of a defect. Threshold 1542a may be used to indicate a defective increase in height, e.g., a "bump", while threshold 1542b may be used to indicate a defective decrease in height, e.g., a "dip". The two thresholds may be chosen, e.g., relative to mid-point or weighted average of Z-height values of all the pixels within a process tools field of view, e.g., within a Lithography Scanner's field, where the "field" is the X-Y area containing a pattern that is printed in one "shot" by the Lithography Scanner with a limited/fixed scanner Depth of Focus. The mid-point may also be the mid-point of an X-Y area that is a subset of the maximum Lithography Scanner's field, e.g., where the Lithography Scanner is able to vary its focus as a subset of the field. The mid-point may also be any other X-Y area as defined by a user (for example a particular area of special interest in terms of the chips pattern). As illustrated, the final relative height of pixel 1516 exceeds threshold 1542a and thus, indicates the presence of "bump" defect 1517 at pixel 1516 and the final relative height of pixel 1514 is below threshold 1542b and thus, indicates the presence of "dip" defect 1515 at pixel 1514.

Graph 1540 additionally illustrates a Depth of Focus window 1544, which also may be used to identify variations in surface height that are outside an acceptable Depth of Focus of a process tool, and therefore may be considered defects. The Depth of Focus window 1544, for example, may similarly be centered on the mid-point or weighted average of Z-height values of all the pixels within a process tools field of view, e.g., within a Lithography Scanner's field or a subset of the maximum Lithography Scanner's field. As illustrated, the final relative heights of both pixels 1514 and 1516 is outside the Depth of Focus window 1544, and thus, may indicate the presence of defects 1515 and 1517 at pixels 1514 and 1516, respectively.

Figure 16:
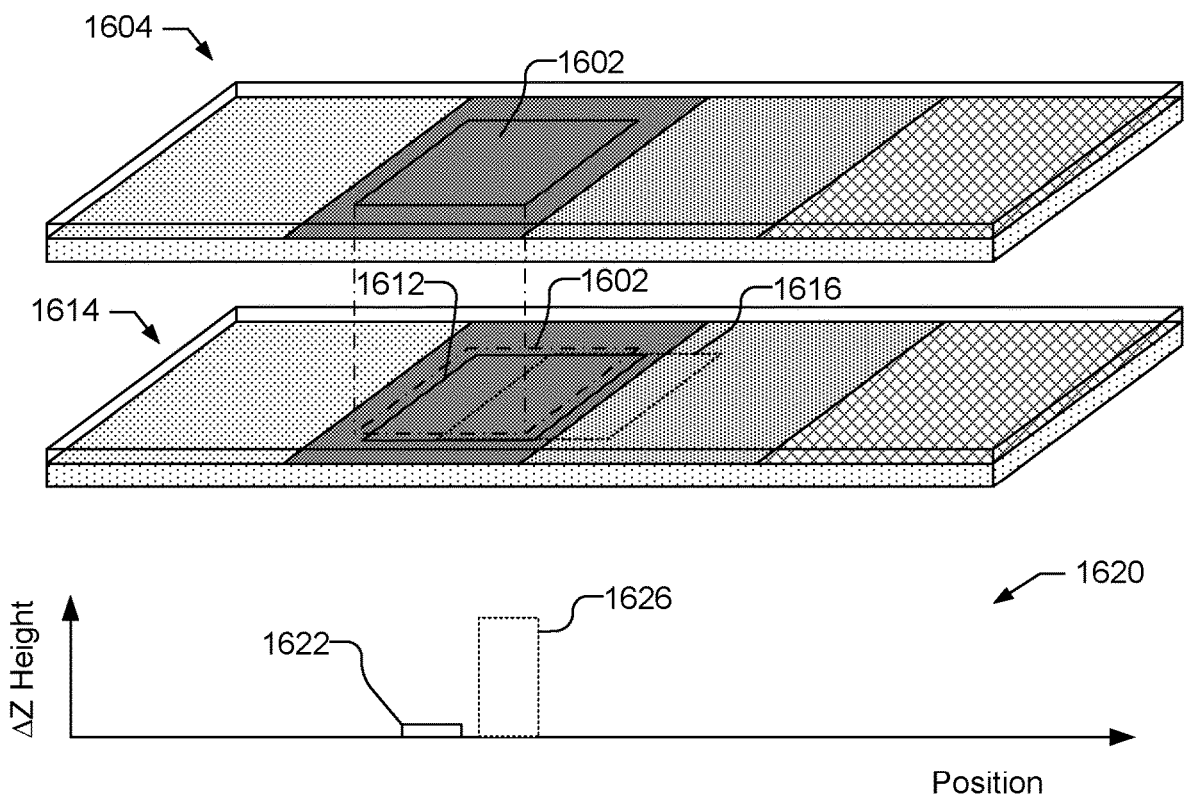
FIG. 16 illustrates corresponding pixels having the same relative positions and shifted relative positions and the effects on the measured height difference.

FIG. 16 illustrates corresponding pixels having the same relative positions, e.g., die-to-die across the sample and within-die, or having different within-die positions but have the same underlying pattern, and shifted relative positions and the effects on the measured height difference. FIG. 16 illustrates for example, shows a single reference pixel 1602 measured on a portion of a reference sample 1604 having multiple patterns under an at least partially transparent film. FIG. 16 further illustrates a portion of a test sample 1614 that is nominally the same as the reference sample 1604 and shows the single reference pixel 1602 from the reference sample 1604 projected onto the surface of the test sample 1614 with dot-dash lines. A first test pixel 1612 that has substantially, but not precisely, the same relative position as the reference pixel 1602 is illustrated with solid lines and a second text pixel 1616 that is significantly shifted with respect to the reference pixel 1602 is shown with dotted lines. A graph 1620 in FIG. 16 illustrates a height difference (ΔZ height) between the reference pixel 1602 and the first test pixel 1612 with a solid bar 1622 and the second test pixel 1616 with dotted lines. As can be seen, the first test pixel 1612 is slightly shifted with respect to the reference pixel 1602 but has the same underlying pattern and, accordingly, the measured height is strongly correlated to the actual height differences at these pixels, as indicated by the relatively small bar 1622. The second test pixel 1616, however, is shifted significantly with respect to the reference pixel 1602 such that it includes a portion of a different underlying pattern and, accordingly, the height difference is not strongly correlated to the actual height differences at these pixels, as indicated by the relatively large bar 1626. Thus, it can be seen that the corresponding pixels should be measured from same relative positions so that the underlying patterns are the same and effects of the underlying patterns on the measured surface height are constant and can be ignored. Decreases in XY precision will decrease the accuracy of the topology signal, and increase the noise in the measurement (due to differences in the underlying pattern). For example a 10% difference in relative pixel XY placement will cause a relatively small drop in signal and rise in noise, whereas an XY placement error between two pixels of 90% of a pixel width will mean most of the signal is lost, and most of the measurement will be noise. The degree to which XY relative placement accuracy impacts signal depends on how similar or different the pattern is surrounding the pixel (vs inside the pixel). Thus, the acceptable precision may depend, e.g., on the pixel size as well as the dimensions, e.g., pitch, of the underlying patterns, by may be, e.g., +/−10%, +/−20%, +/−30%, +/−40%, or +/−50% of the pixel size in each of the XY dimensions.

Decreases in XY precision will decrease the accuracy of the topology signal, and increase the noise in the measurement (due to differences in the underlying pattern). For example a 10% difference in relative pixel XY placement will cause a relatively small drop in signal and rise in noise, whereas an XY placement error between two pixels of 90% of a pixel width will mean most of the signal is lost, and most of the measurement will be noise. The degree to which XY relative placement accuracy impacts signal depends on how similar or different the pattern is surrounding the pixel (vs inside the pixel).

Figure 17:
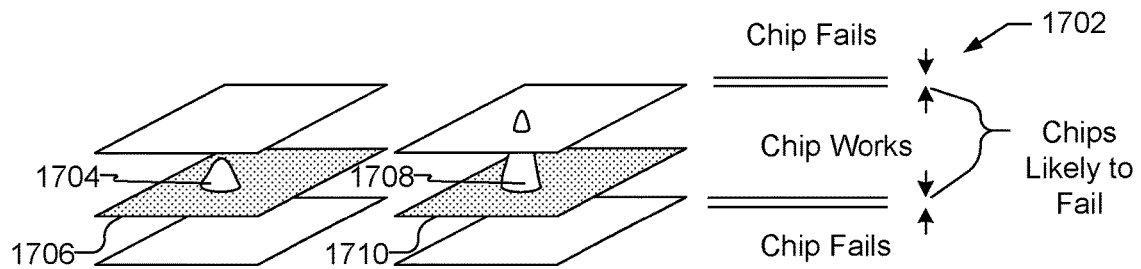
FIG. 17 illustrates a Depth of Focus window of a process tool and the effects of different defects on a sample.

FIG. 17, by way of example, illustrates a Depth of Focus window 1702 and the need to determine when a height defect is outside the Depth of Focus. As illustrated, a defect 1704 may be present on the surface 1706 of a sample, but the surface height of the defect may be within the Depth of Focus window. Thus, even though a defect 1704 is present, the resulting chip will likely be functional. On the other hand, defect 1708 on surface 1710 has a surface height that exceeds the Depth of Focus window, and thus, will likely cause the resulting chip to fail. As illustrated, the Depth of Focus window 1702 may indicate heights where resulting chips will work or fail, and may also indicate heights where failure of the chips is likely but not certain.

Figure 18:
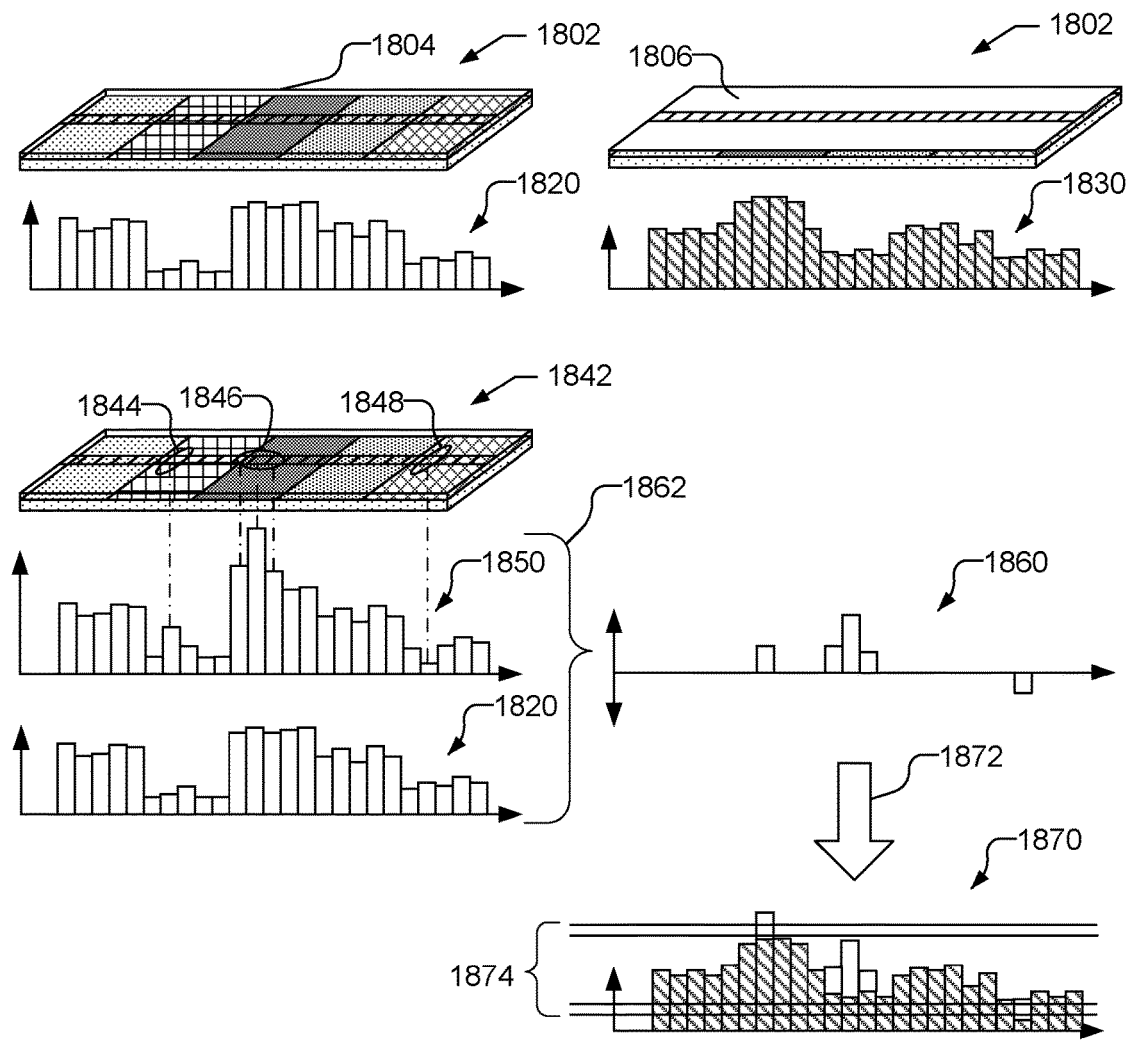
FIG. 18 illustrates an example of determining a proxy surface topography of a test sample with an at least partially transparent surface layer using surface topography measurements from a reference sample before and after deposition of an opaque film.

FIG. 18 is another example of determining a proxy surface topography of a test sample. As illustrated, surface topographies 1820 and 1830, e.g., relative heights at a plurality of positions (or pixels) of a reference sample 1802 are respectively measured before and after deposition of an opaque film 1806 over an at least partially transparent surface film 1804. The surface topography 1850 of a test sample 1842, which is nominally the same as the reference sample (prior to deposition of the opaque film 1806), is similarly measured, e.g., as relative heights at a plurality of positions that correspond to the positions on the reference sample 1802 that were measured. As illustrated, the test sample 1842 may include a number of detects 1844, 1846, and 1848 that are not present on the reference sample 1802.

As illustrated by bracket 1862, the surface topography 1850 of the test sample 1842 is compared to the pre-opaque film surface topography 1820 of the reference sample 1802 resulting in the differential surface topology 1860, which is the height difference at the plurality of positions on the test sample 1842 and reference sample 1802. As illustrated by arrow 1872, the differential surface topology 1860 and the post-opaque film surface topography 1830 of the reference sample 1802 are combined to produce the proxy surface topography 1870 of the test sample 1842. The relative height at each pixel in the proxy surface topography 1870 may be compared to a Depth of Focus window 1874 (or a predetermined height threshold) to determine if any position on the test sample 1842 has a relative height that is outside the Depth of Focus window and is therefore indicated as being a defect. As can be seen, defect 1844 produces a relative height that is outside the Depth of Focus window 1874 and is therefore indicated as a defect. Defect 1846, on the other hand, is relatively larger than defect 1844 and produces a greater height difference in the differential surface topography 1860, but is inside the Depth of Focus window 1874 and therefore need not be indicated as being a defect. Accordingly, on "killer" defects, i.e., defects that will result in failure of a resulting chip are identified.

Figure 19:
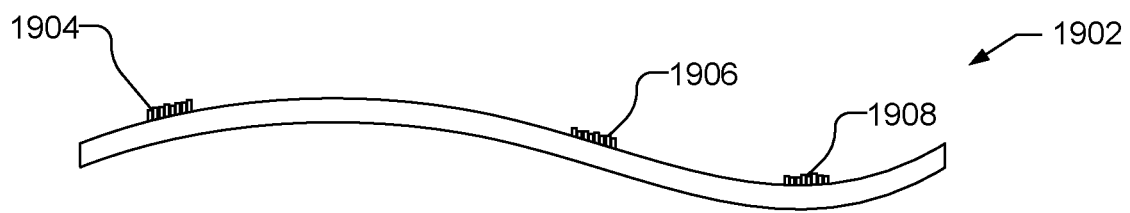
FIG. 19 illustrates a curved test sample and determining a characteristic of the test sample using the proxy surface topography.

The proxy surface topography of the test sample may be used to determine characteristics of the test sample other than defects. For example, FIG. 19 illustrates a test sample 1902 that is non-flat. The proxy surface topography of the test sample 1902 is illustrated with bars in multiple locations 1904, 1906, and 1908 of the test sample 1902. If desired, the proxy surface topography may be measured over the entirety of the test sample 1902 or may be measured in select locations, as illustrated in FIG. 19, to improve throughput. The relative proxy surface heights for all measured pixels on the test sample 1902 may be combined together and could be combined with measurements from other tools, e.g., using a best fit curve or other statistical method, and used to measure characteristics, such as bow, warp, total thickness variation, total indicated reading, spherical reference measurement, as well as the large scale and/or micro-scale 3D surface topology, including local focal plane deviation and local thickness variation, of the test sample 1902.

Moreover, the resulting proxy surface topography 1870 of the test sample 1842 or relative heights at select pixels in the proxy surface topography 1870 may be analyzed separately, i.e., separately from defect detection, to characterize one or more parameters of the test sample 1842. Additionally, the optical metrology device or other metrology devices may perform additional measurements on the reference sample 1802 and/or the test sample 1842 at the same positions used to determine the surface topography. For example, Optical Spectra CD (OCD) & Film Metrology (OFM), atomic force microscopy (AFM), etc., measurements may be performed. The additionally collected measurements may provide additional analysis capability with the proxy surface topography 1870. By way of example, other metrology measurements may reduce any residual errors in relative Z-height data for different XY positions. If an "absolute Z height" can be determined, e.g., relative to a fixed surface such as the chuck surface, then other measurements may act as an anchor point to enable an "absolute Z height" output. In one aspect, OFM measurements of the test sample 1842 may be used prior to measurement of the surface topography in order to identify areas where inspection is desirable. Thus, the relatively slower surface topography measurements of the test sample may be reduced to specifically identified areas instead of the entire test sample.

The relative height at each pixel in the proxy surface topography 1870 and/or the characteristic of the test sample, such as a value of the measured parameter, e.g., bow or warp, or an indication of a defect (including position if desired), may be communicated from the optical metrology tool to a process tool that causes the process tool to adjust a process parameter associated with a fabrication process step of the semiconductor wafer fabrication sequence for the test sample 1842 (feed forward) or for subsequently processed samples (feedback) based on the indication of relative height or defect. By way of example and not limitation, after receiving the data, a Lithography process tool may alter its focal position(s) used on the test sample or subsequent samples or a CMP polishing tool may change parameters, such as the duration and pressure, applied during the polishing process of subsequent samples or the same test sample if taken back for additional polishing.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of characterizing a test sample that is a semiconductor sample, the method comprising:
    measuring with an optical metrology device a first surface topography of at least one reference sample having a surface film that is at least partially transparent to one or more wavelengths of light used by the optical metrology device, wherein the first surface topography comprises a first relative height of a top surface of the at least one reference sample at each measurement position in a first plurality of measurement positions on the at least one reference sample;
    measuring with the optical metrology device a second surface topography of the at least one reference sample after an opaque film is deposited over the surface film, wherein the opaque film is opaque to the one or more wavelengths of light used by the optical metrology device, wherein the second surface topography comprises a second relative height of the top surface of the at least one reference sample at each measurement position in the first plurality of measurement positions;
    storing the first surface topography and the second surface topography of the at least one reference sample and a position of each measurement position in the first plurality of measurement positions on the at least one reference sample;
    measuring with the optical metrology device a third surface topography of the test sample, wherein the test sample is nominally the same as the at least one reference sample and includes a surface film that is at least partially transparent to the one or more wavelengths of light used by the optical metrology device and does not include an opaque film deposited over the surface film, wherein the third surface topography comprises a third relative height of a top surface of the test sample at each measurement position in a second plurality of measurement positions on the test sample, wherein a position of each measurement position in the second plurality of measurement positions on the test sample is the same as the position of each measurement position in the first plurality of measurement positions on the at least one reference sample;
    determining a differential surface topography by comparing the first surface topography to the third surface topography;
    determining a proxy surface topography of the test sample by combining the differential surface topography with the second surface topography, wherein the proxy surface topography comprises a fourth relative height of the top surface of the test sample at each measurement position in the second plurality of measurement positions on the test sample;

determining a characteristic of the test sample with the proxy surface topography of the test sample; and communicating a signal to a process tool that causes the process tool to adjust a process parameter associated with a fabrication process step of a sample fabrication sequence based on the characteristic of the test sample.

2. The method of claim 1, wherein determining the characteristic of the test sample with the proxy surface topography of the test sample comprises using the proxy surface topography of the test sample to detect defects on the test sample.

3. The method of claim 2, wherein using the proxy surface topography of the test sample to detect defects on the test sample comprises:

comparing the fourth relative height at each measurement position in the second plurality of measurement positions to a predetermined threshold height;

providing an indication that the test sample includes a defect when the fourth relative height of any measurement position is greater than the predetermined threshold height.

4. The method of claim 2, wherein using the proxy surface topography of the test sample to detect defects on the test sample comprises:

comparing the fourth relative height at each measurement position in the second plurality of measurement positions to a Depth of Focus window for a processing tool; and providing an indication that the test sample includes a defect when the fourth relative height of any measurement position is outside the Depth of Focus window.

5. The method of claim 1, wherein determining the characteristic of the test sample with the proxy surface topography of the test sample comprises using the proxy surface topography of the test sample to measure at least one of warp, bow, large scale three-dimensional (3D) surface topology, micro-scale 3D surface topology, or a combination thereof.

6. The method of claim 1, wherein determining the differential surface topography comprises determining a height difference between the first relative height at each measurement position in the first plurality of measurement positions in the first surface topography and the third relative height at each corresponding measurement position in the second plurality of measurement positions in the third surface topography.

7. The method of claim 6, wherein determining the proxy surface topography of the test sample by combining the differential surface topography with the second surface topography comprises combining the height difference at each measurement position in the second plurality of measurement positions on the test sample and the second relative height at each corresponding measurement position in the first plurality of measurement positions on the at least one reference sample.

8. The method of claim 1, wherein the first relative height at each measurement position in the first plurality of measurement positions provided by the first surface topography is at least partially dependent on one or more patterns underlying the surface film of the at least one reference sample and the third relative height at each measurement position in the second plurality of measurement positions provided by the third surface topography is at least partially dependent on one or more patterns underlying the surface film on the test sample.

9. The method of claim 8, wherein the second relative height at each measurement position in the first plurality of measurement positions provided by the second surface topography is not dependent on the one or more patterns underlying the surface film and the opaque film of the at least one reference sample.

10. The method of claim 1, wherein multiple reference samples are used to measure the first surface topography and the second surface topography, wherein surface topographies are measured from the multiple reference samples and statistically combined to produce the first surface topography and the second surface topography.

11. An optical metrology apparatus configured to characterize a test sample that is a semiconductor sample, the optical metrology apparatus comprising:

a light source that produces an illumination beam;

an objective lens that directs the illumination beam to be incident on the test sample and to receive light reflected by the test sample;

at least one detector array that receives the light after it is reflected by the test sample and acquires optical metrology data from the light; and at least one processor coupled to the at least one detector array and is configured to receive the optical metrology data, the at least one processor configured to:

obtain a first surface topography of at least one reference sample and a second surface topography of the at least one reference sample, wherein the at least one reference sample has a surface film that is at least partially transparent to one or more wavelengths of light in the illumination beam, the first surface topography comprises a first relative height of a top surface of the at least one reference sample at each measurement position in a first plurality of measurement positions on the at least one reference sample, and the second surface topography of the at least one reference sample comprises a second relative height of the top surface of the at least one reference sample at each measurement position in the first plurality of measurement positions after an opaque film is deposited over the surface film, wherein the opaque film is opaque to the one or more wavelengths of light used by the optical metrology apparatus;

determine a third surface topography of the test sample from the optical metrology data, wherein the test sample is nominally the same as the at least one reference sample and includes a surface film that is at least partially transparent to the one or more wavelengths of light in the illumination beam and does not include an opaque film deposited over the surface film, wherein the third surface topography comprises a third relative height of a top surface of the test sample at each measurement position in a second plurality of measurement positions on the test sample, wherein a position of each measurement position in the second plurality of measurement positions on the test sample is the same as the position of each measurement position in the first plurality of measurement positions on the at least one reference sample;

determine a differential surface topography by comparing the first surface topography to the third surface topography;

determine a proxy surface topography of the test sample by combining the differential surface topography with the second surface topography, wherein the proxy surface topography comprises a fourth relative height of the top surface of the test sample at each measurement position in the second plurality of measurement positions on the test sample;

determine a characteristic of the test sample with the proxy surface topography of the test sample; and communicate a signal to a process tool that causes the process tool to adjust a process parameter associated with a fabrication process step of a sample fabrication sequence based on the characteristic of the test sample.

12. The optical metrology apparatus of claim 11, wherein the first surface topography and the second surface topography are measured by a separate optical metrology apparatus and are stored and obtained from a memory in the optical metrology apparatus.

13. The optical metrology apparatus of claim 11, wherein the first surface topography and the second surface topography are determined by the least one processor from optical metrology data acquired by the at least one detector array from the reference sample.

14. The optical metrology apparatus of claim 11, wherein the at least one processor is configured to determine the characteristic of the test sample with the proxy surface topography of the test sample by being configured to use the proxy surface topography of the test sample to detect defects on the test sample.

15. The optical metrology apparatus of claim 14, wherein the at least one processor is configured to use the proxy surface topography of the test sample to detect defects on the test sample by being configured to:
compare the fourth relative height at each measurement position in the second plurality of measurement positions to a predetermined threshold height;
provide an indication that the test sample includes a defect when the fourth relative height of any measurement position is greater than the predetermined threshold height.

16. The optical metrology apparatus of claim 14, wherein the at least one processor is configured to use the proxy surface topography of the test sample to detect defects on the test sample by being configured to:
compare the fourth relative height at each measurement position in the second plurality of measurement positions to a Depth of Focus window for a processing tool; and
provide an indication that the test sample includes a defect when the fourth relative height of any measurement position is outside the Depth of Focus window.

17. The optical metrology apparatus of claim 11, wherein the at least one processor is configured to determine the characteristic of the test sample with the proxy surface topography of the test sample by being configured to use the proxy surface topography of the test sample to measure at least one of warp, bow, large scale three-dimensional (3D) surface topology, micro-scale 3D surface topology, or a combination thereof.

18. The optical metrology apparatus of claim 11, wherein the at least one processor is configured to determine the determine the differential surface topography by comparing the first surface topography to the third surface topography by being configured to determine a height difference between the first relative height at each measurement position in the first plurality of measurement positions in the first surface topography and the third relative height at each corresponding measurement position in the second plurality of measurement positions in the third surface topography.

19. The optical metrology apparatus of claim 11, wherein the at least one processor is configured to determine the proxy surface topography of the test sample by combining the differential surface topography with the second surface topography by being configured to combine the height difference at each measurement position in the second plurality of measurement positions on the test sample and the second relative height at each corresponding measurement position in the first plurality of measurement positions on the at least one reference sample.

20. The optical metrology apparatus of claim 11, wherein the first relative height at each measurement position in the first plurality of measurement positions provided by the first surface topography is at least partially dependent on one or more patterns underlying the surface film of the at least one reference sample and the third relative height at each measurement position in the second plurality of measurement positions provided by the third surface topography is at least partially dependent on one or more patterns underlying the surface film on the test sample.

21. The optical metrology apparatus of claim 19, wherein the second relative height at each measurement position in the first plurality of measurement positions provided by the second surface topography is not dependent on the one or more patterns underlying the surface film and the opaque film of the at least one reference sample.

22. The optical metrology apparatus of claim 11, wherein multiple reference samples are used to measure the first surface topography and the second surface topography, wherein surface topographies are measured from the multiple reference samples and statistically combined to produce the first surface topography and the second surface topography.

23. The optical metrology apparatus of claim 11, wherein the optical metrology apparatus is an interferometer.

* * * * *